(12) United States Patent
Kropf

(10) Patent No.: US 9,949,022 B2
(45) Date of Patent: Apr. 17, 2018

(54) UNDERWATER COMMUNICATION SYSTEMS, UNDERWATER SPEAKERS, UNDERWATER MICROPHONE ASSEMBLIES AND METHODS

(71) Applicant: Keith Kropf, Key Largo, FL (US)

(72) Inventor: Keith Kropf, Key Largo, FL (US)

( * ) Notice: Subject to any disclaimer, the term of this patent is extended or adjusted under 35 U.S.C. 154(b) by 0 days.

(21) Appl. No.: 14/868,139

(22) Filed: Sep. 28, 2015

(65) Prior Publication Data

US 2016/0094911 A1  Mar. 31, 2016

Related U.S. Application Data

(60) Provisional application No. 62/056,736, filed on Sep. 29, 2014.

(51) Int. Cl.
*H04R 1/44* (2006.01)
*A61B 50/30* (2016.01)

(52) U.S. Cl.
CPC ........ *H04R 1/44* (2013.01); *A61B 2050/3014* (2016.02)

(58) Field of Classification Search
CPC ............................................ A61B 2050/3014
USPC .................. 367/131–132; 381/334, 387–389
See application file for complete search history.

(56) References Cited

U.S. PATENT DOCUMENTS

| 945,929 | A | 1/1910 | Gager |
| 1,418,388 | A | 6/1922 | Miessner |
| 1,771,774 | A | 7/1930 | Cox |
| 2,844,212 | A | 7/1958 | Hogan et al. |
| 3,123,680 | A | 3/1964 | Minton, Jr. et al. |
| 3,174,129 | A * | 3/1965 | Laughlin ................ H04B 11/00 128/201.19 |
| 3,210,723 | A | 10/1965 | Martelli et al. |
| 3,461,910 | A | 8/1969 | Selsam et al. |
| 3,670,299 | A | 6/1972 | Kahn |
| 3,828,887 | A | 8/1974 | Alexander |

(Continued)

FOREIGN PATENT DOCUMENTS

| GB | 1915 08424 | 3/1916 |
| JP | H08-19079 | 1/1996 |

(Continued)

OTHER PUBLICATIONS

WO PCT/US2015/052727 Search Rept., dated Jan. 11, 2016, Kropf.

(Continued)

*Primary Examiner* — Disler Paul
(74) *Attorney, Agent, or Firm* — Wells St. John P.S.

(57) ABSTRACT

Underwater communication systems, underwater speakers, underwater microphone assemblies and associated methods are described. According to one aspect, an underwater speaker includes a housing, a transducer member coupled with the housing and positioned to contact a body of water, wherein the transducer member is configured to vibrate to generate sound pressure waves within the body of water which comprise content which is audible to humans within the body of water, and an exciter coupled with the transducer member and configured to impart forces to the transducer member to cause the vibration of the transducer member to generate the sound pressure waves in the body of water as result of a received electrical signal which comprises the content.

10 Claims, 17 Drawing Sheets

(56) References Cited

U.S. PATENT DOCUMENTS

| | | | |
|---|---|---|---|
| 3,993,973 A | | 11/1976 | Hutchins et al. |
| 4,183,422 A | | 1/1980 | Williams |
| 4,414,851 A | | 11/1983 | Maglic |
| 4,485,272 A | * | 11/1984 | Duong .................. H04M 9/08 |
| | | | 379/388.07 |
| 4,527,657 A | | 7/1985 | Payne |
| 4,763,307 A | | 8/1988 | Massa |
| 4,839,871 A | | 6/1989 | Massey |
| 5,825,718 A | * | 10/1998 | Ueki ...................... H04B 11/00 |
| | | | 367/132 |
| 8,006,320 B1 | | 8/2011 | Rohbani |
| 2003/0123692 A1 | * | 7/2003 | Ueki ....................... H04R 1/44 |
| | | | 381/398 |
| 2004/0182641 A1 | | 9/2004 | Overmyer |
| 2006/0140421 A1 | * | 6/2006 | Swafford ............... A01K 85/01 |
| | | | 381/124 |
| 2008/0298177 A1 | | 12/2008 | Giles et al. |
| 2010/0284553 A1 | | 11/2010 | Conti et al. |
| 2012/0256867 A1 | * | 10/2012 | Annacone .............. G06F 3/044 |
| | | | 345/174 |
| 2016/0094912 A1 | | 3/2016 | Kropf |

FOREIGN PATENT DOCUMENTS

| | | |
|---|---|---|
| JP | 3295680 A | 6/2002 |
| WO | WO 2012/095780 | 7/2012 |
| WO | PCT/US2015/052727 | 4/2017 |

OTHER PUBLICATIONS

WO PCT/US2015/052727 Writ. Opin., dated Jan. 11, 2016, Kropf.
WO PCT/US2016/024156 Search Rept., dated Jul. 22, 2016, Keith Kropf.
WO PCT/US2016/024156 Writ. Opin., dated Jul. 22, 2016, Keith Kropf.
Kropf, U.S. Appl. No. 62/056,736, filed Sep. 29, 2014, titled "Underwater Communication Devices and Methods", 25 pages.
Kropf, U.S. Appl. No. 62/194,130, filed Jul. 17, 2015, titled "Underwater Voice Communication Device", 10 pages.
Coomber Electronic Equipment Ltd., "1932 Underwater Loudspeaker", available online at http://www.coomberaudio.com/equipment/details/Speakers/1932-Underwater-Loudspeaker.html, Oct. 7, 2013, 5 pages.
Clerk Synthesis, Inc., "Diluvio™ Underwater Speaker" and brochure, available online at http://clarksynthesis.com/ clark-synthesis-products/diluvio-underwater-speaker/, Sep. 19, 2014, 3 pages.
DiveSCULS, "About SCULS", available online at http://divesculsnet.domain.com:80/about/, May 25, 2014, 2 pages.
DiveSCULS, "SCULS Self Contained Underwater Loud Speaker", available online at http://divesculsnet.domain.com:80/products-page/product-category/sculs/, May 25, 2014, 1 page.
Lubell Labs Inc., "Clark Synthesis AQ339 Aquasonic Underwater Speaker", available online at http://lubell.com/AQ339.html, Sep. 22, 2013, 1 page.
Lubell Labs Inc., "EV UW30 Underwater Speaker for Marine Biology", available online at http://lubell.com/UW30.html, Dec. 12, 2013, 2 pages.
Lubell Labs Inc., "LL916C Underwater Speaker", available online at http://lubell.com/LL916.html, Dec. 3, 2013, 1 page.
Lubell Labs Inc., "LL916H & LL916C Pistonic Piezoelectric Underswater Speakers" available online at http://lubell.com/LL916.html, Feb. 21, 2016, 2 pages.
Navy, "Voicepipes and Speaking-Tubes", 2010, 2 pages.
Ocean Reef Group, "GSM G.DIVERS", available online at http://diving.oceanreefgroup.com/accessory/gsm-g-divers/, Feb. 25, 2017, 2 pages.
Ocean Technology Systems, "Buddy Phone Through-Water Tranceivers (1/2 Watt Output Power)", available online at http://ots.mwrc.net/en/product.php?product_id=44767, Dec. 25, 2015, 4 pages.
Ocean Technology Systems, "EM-OTS2 for Guardian FFM", available online at http://ots.mwrc.net/en/product.php?product_id=44547, Jun. 23, 2012, 3 pages.
Ocean Technology Systems, "ME-16R Hot Mic (150 Ohm)", available online at http://ots.mwrc.net/en/product.php?product_id=43905, Apr. 28, 2016, 3 pages.
Oceanears, "Underwater Speaker DRS-8", available online at http://oceanears.com/drs-8-underwater-speaker/, Oct. 25, 2015, 4 pages.
Uetax, "Underwater Speaker UA30, UA40, UA50, UA60", available online at http://uetax.co.jp/hpj/products/en/en-underwater-speaker/, Feb. 25, 2017, 1 page.
Yamagata Casino Co., Ltd., "Logosease", available online at http://logosease.yamagata-casio.co.jp/en/product/, May 10, 2013, 2 pages.
Techwalla, "How to Waterproof Headphones", available online at https://www.techwalla.com/articles/how-to-waterproof-headphones, Mar. 31, 2015, 3 pages.

* cited by examiner

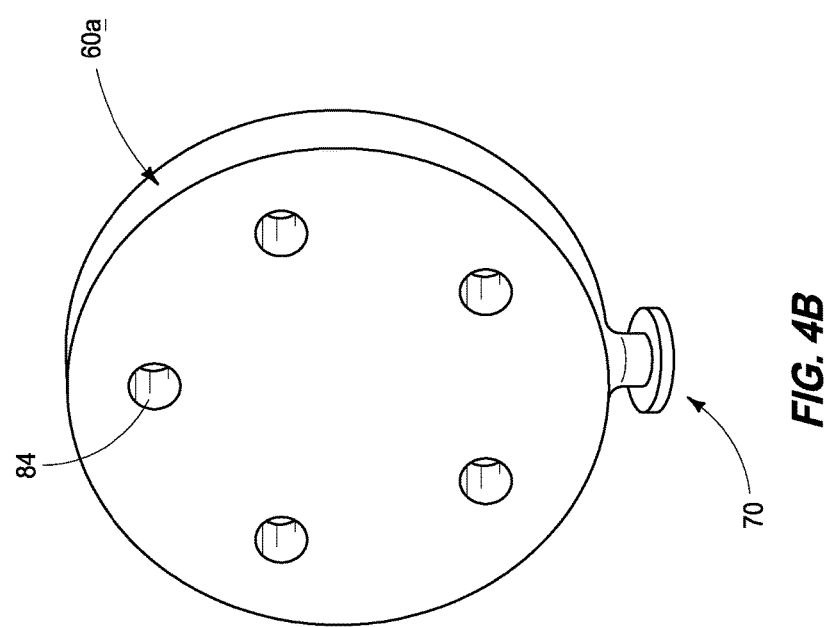

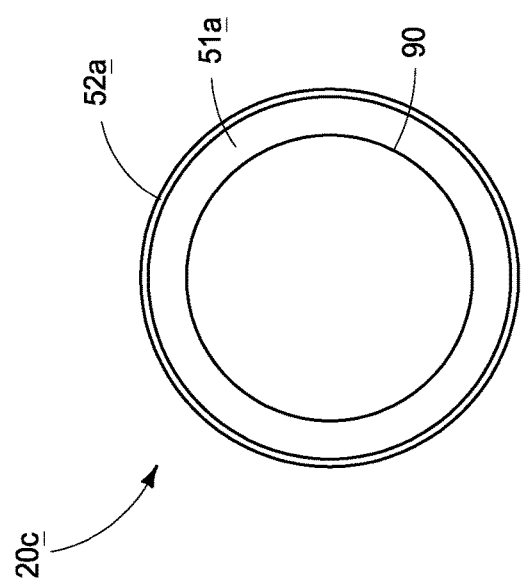

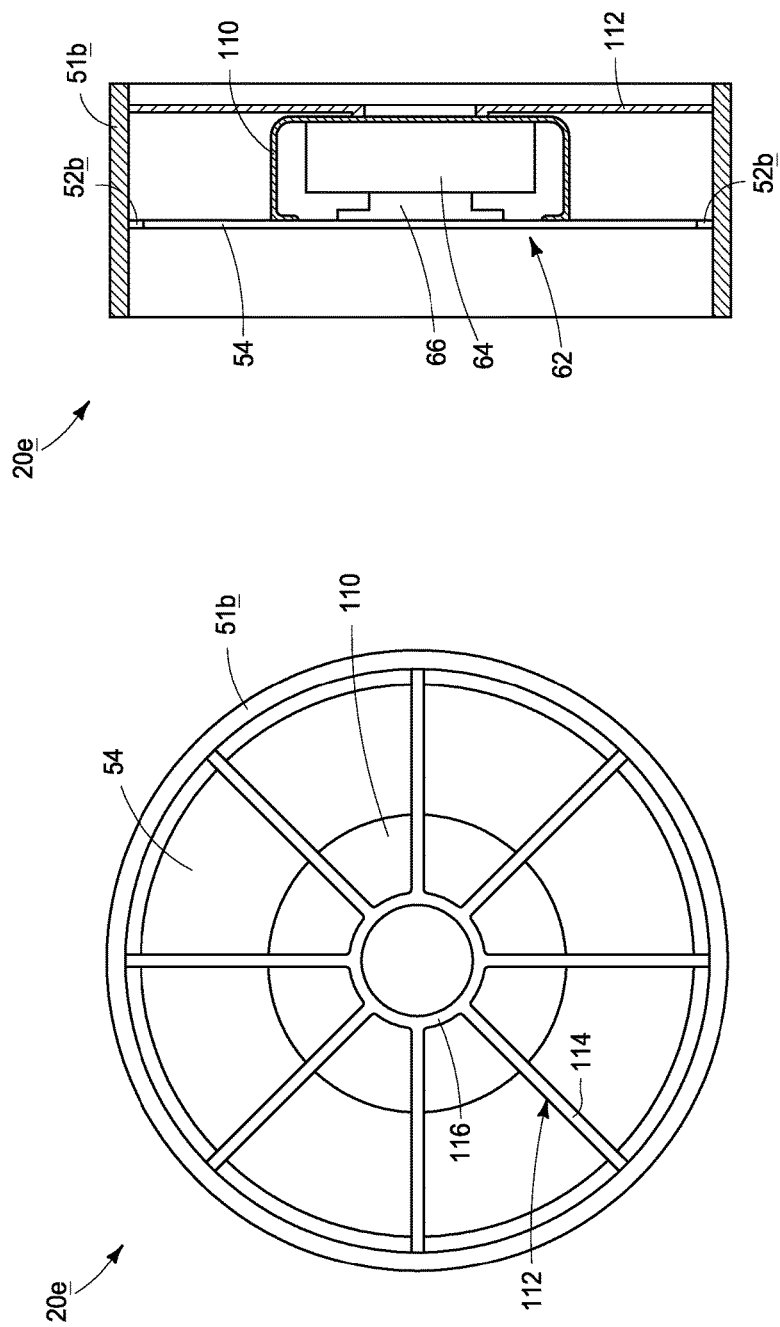

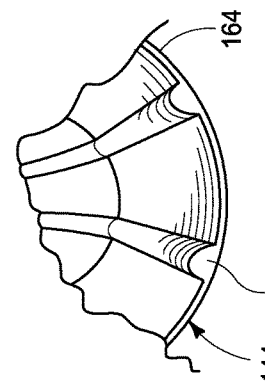
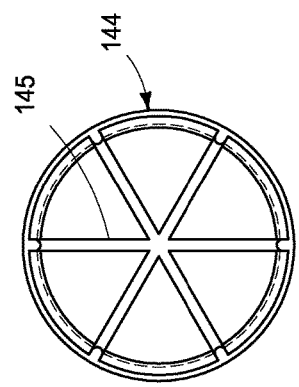
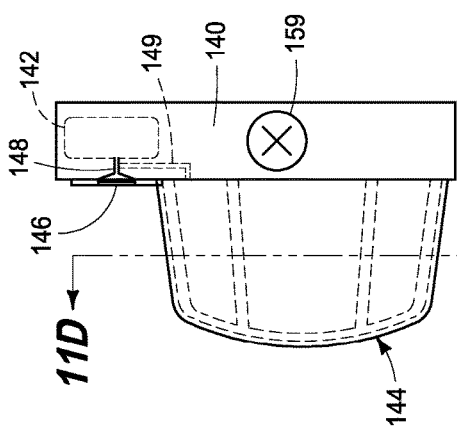
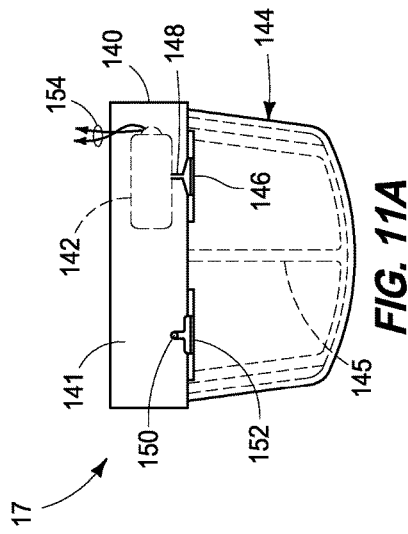
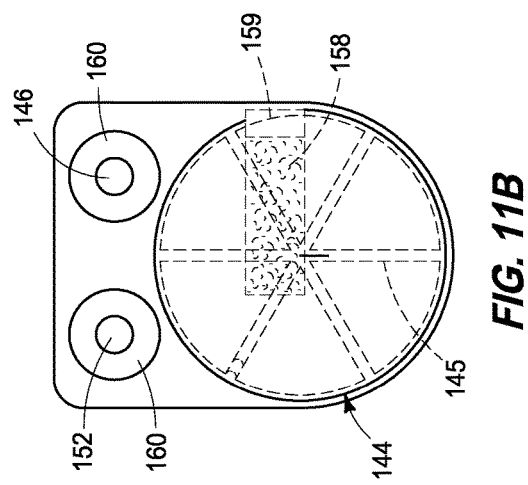

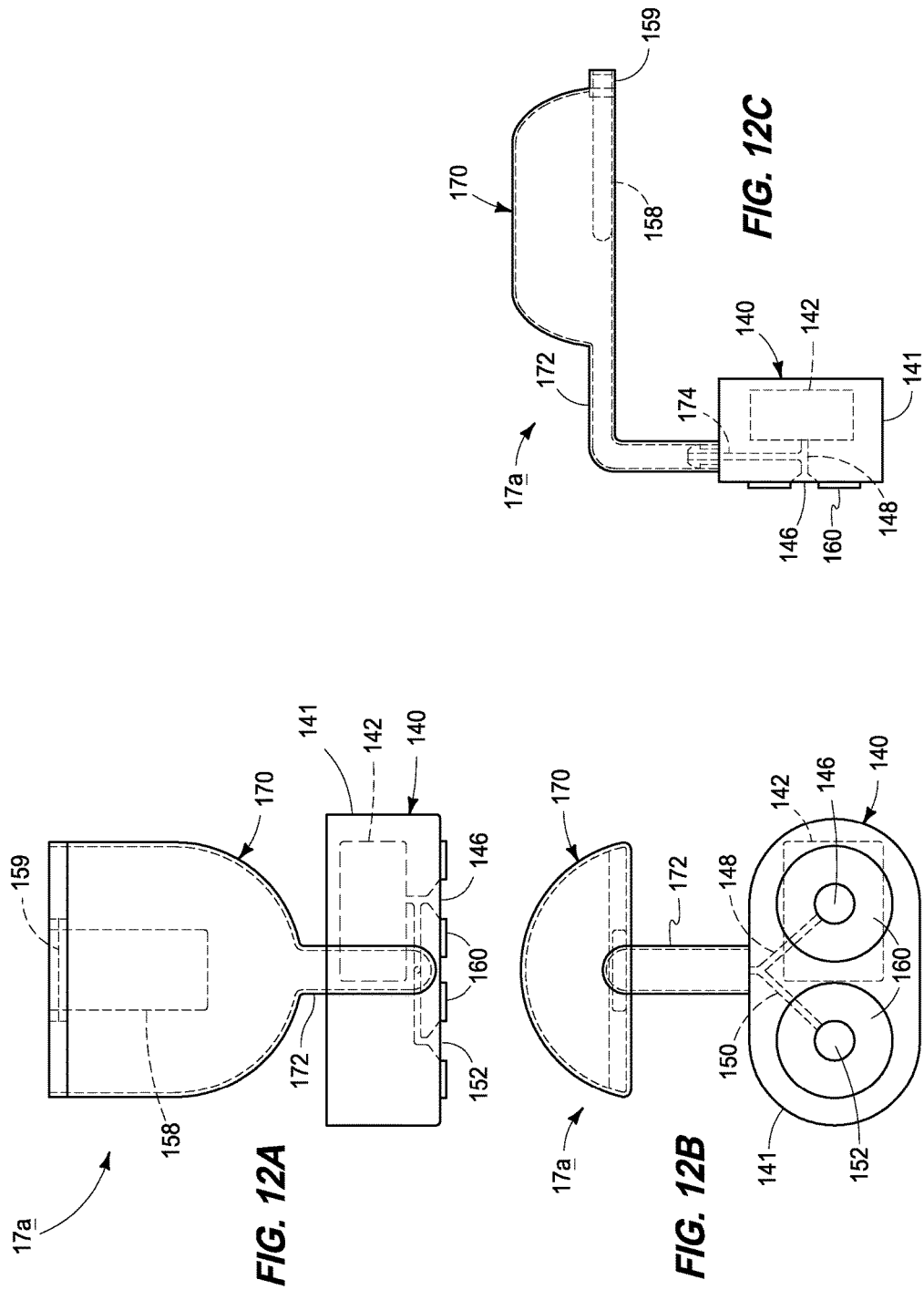

UNDERWATER COMMUNICATION SYSTEMS, UNDERWATER SPEAKERS, UNDERWATER MICROPHONE ASSEMBLIES AND METHODS

RELATED PATENT DATA

This application claims the benefit of and priority to U.S. Provisional Patent Application Ser. No. 62/056,736 filed Sep. 29, 2014, titled "Underwater Communication Devices and Methods," the disclosure of which is incorporated herein by reference.

TECHNICAL FIELD

This disclosure relates to underwater communication systems, underwater speakers, underwater microphone assemblies and associated methods.

BACKGROUND OF THE DISCLOSURE

Scuba diving is not regulated in the US by any government agencies. The industry has adopted certification requirements for divers and is self-regulating. The recommended maximum diving depth for a "recreational diver" is 130 feet. Technical divers and commercial divers do dive to deeper depths (approaching 1000 ft.) using special air mixes and equipment.

At sea level, the atmospheric pressure varies slightly, but is about 14.7 pounds per square inch, or more conveniently 1 atmosphere (1 atm). When descending into water, the pressure down at 33 feet in sea water, or 34 feet in fresh water, increases by an additional atmosphere, so the pressure is 2 atm. The increase in pressure is a linear function, so at 66 feet, the pressure is 3 atm, etc. The pressure at 130 feet is about 5 atm, or about 75 psi.

Most recreational divers breathe from a "regulator" that is held in the mouth by biting down on a mouthpiece. The regulator is attached to a tank of compressed air. Most divers are taught from the very beginning classes to take their regulator out of their mouth and throw it to the side, simulating having the regulator pulled out of their mouth. They are instructed to retrieve it and put it back in their mouth. Most everyone has no trouble with this task. This skill is required for a diver to gain certification.

Divers typically wear a buoyancy compensation device (commonly called a BCD) which is an inflatable vest that is connected to the air tank, and is used to adjust buoyancy. Most divers also attach other equipment to their BCD, such as regulator gauges, knives, safety sausages, topside signaling devices, dive slates for written communication, etc. Underwater communication system described in the disclosure below may be connected to the BCD with a retractable lanyard in some embodiments.

At least some embodiments of the disclosure described below are directed to underwater communication systems, underwater speakers, underwater microphone assemblies and associated methods.

BRIEF DESCRIPTION OF THE DRAWINGS

Example embodiments of the disclosure are described below with reference to the following accompanying drawings.

FIG. 4B is a perspective view of a bladder of the speaker assembly according to the second embodiment.

FIG. 5A is a rear view of a speaker assembly according to a third embodiment.

FIG. 7A is a rear view of a speaker assembly according to a fifth embodiment.

FIG. 7B is a sectional view of the speaker assembly according to the fifth embodiment.

FIG. 11A is a top view of a microphone assembly according to a first embodiment.

FIG. 11B is a front view of the microphone assembly according to the first embodiment.

FIG. 11C is a side view of the microphone assembly according to the first embodiment.

FIG. 11D is a sectional view of the microphone assembly according to the first embodiment.

FIG. 11E is a perspective view of a collapsible air chamber of the microphone assembly according to the first embodiment.

FIG. 12A is a top view of a microphone assembly according to a second embodiment.

FIG. 12B is a front view of the microphone assembly according to the second embodiment.

FIG. 12C is a side view of the microphone assembly according to the second embodiment.

DETAILED DESCRIPTION OF THE DISCLOSURE

This disclosure is submitted in furtherance of the constitutional purposes of the U.S. Patent Laws "to promote the progress of science and useful arts" (Article 1, Section 8).

At least some aspects of the disclosure are directed to underwater communication systems, underwater speakers, underwater microphone assemblies and associated methods. The systems and speakers generate and communicate audible signals underwater which are perceptible to humans as well as other species in some of the disclosed embodiments. Communications facilitated by apparatus and methods of the present disclosure include human voice, music and other audible signals. Example embodiments of underwater communication systems described below include one or more subsystems, such as a microphone assembly, a voice chamber assembly, associated circuitry, an underwater speaker and a receiver, and a receiver assembly. Some embodiments have a maximum operating depth which is equal to at least the maximum recommended recreational scuba depth of 130 feet. Other embodiments have an increased maximum operating depth.

Accordingly, in some embodiments, a microphone is provided to communicate speech of the diver to other divers in the vicinity. In other embodiments, other audible sources apart from a microphone may be used to generate audible signals which are to be communicated underwater. For example, amplified electrical signals from an external amplifier or external microphone, for example out of the water, may be generated and applied to the underwater speakers disclosed herein for generation of the audible content underwater. In other embodiments, a diver may wear a source of audible content, such as an MP3 player, and the underwater speakers disclosed herein may communicate the audible content, such as music or the human voice, underwater. Other embodiments and implementations are possible.

Figure 1:
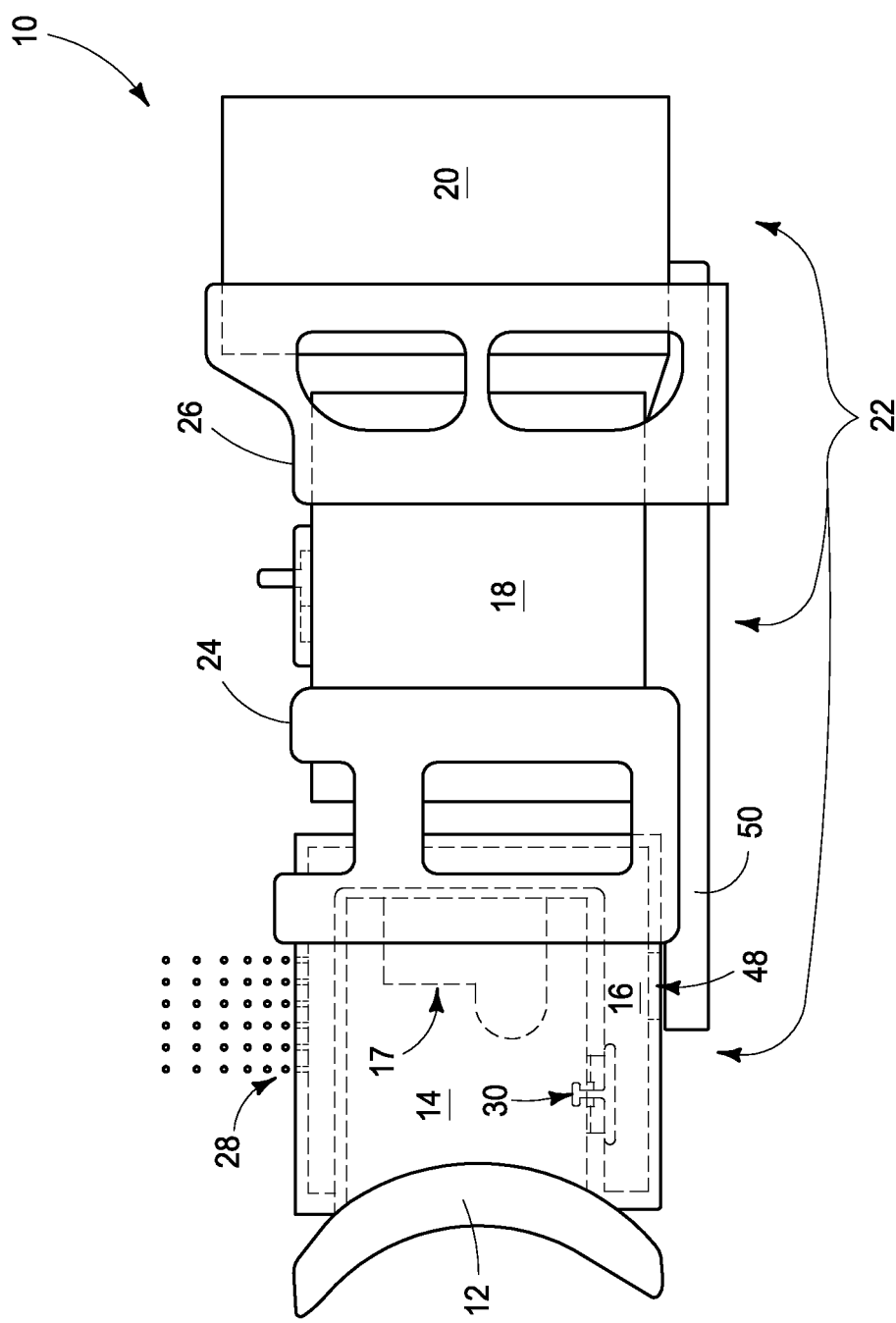
FIG. 1 is a side view of an underwater communication system according to one embodiment.

Referring to FIG. 1, one embodiment of an underwater communication system 10 is shown which operates as an underwater megaphone for use by recreational scuba divers for communication with each other in one application. In one implementation, the communication device is the size of a tennis ball can but the speaker end is slightly larger diameter (8"×3.5") and weighs about two pounds. Other embodiments and applications exist, for example, use of speakers and associated circuitry described herein as underwater pool speakers.

The underwater communication system 10 illustrated in FIG. 1 includes a face seal 12 which is configured to form a seal with a face of the user during use, a voice chamber assembly (including an inner voice chamber 14 and an outer voice chamber 16 in the illustrated example), a microphone assembly 17, circuitry 18, and an underwater speaker 20. The use of two voice chambers 14, 16 helps isolate the microphone assembly 17 from the speaker 20 and reduce feedback. In one implementation, the microphone assembly 17 receives sound pressure waves generated by vocal cords of a user and speaker 20 outputs sound pressure waves into the body of water which correspond to the received sound pressure waves at increased amplitudes.

In one embodiment, the voice chambers 14, 16 are defined by a double wall 42 of sound absorbing material, such as rubber. The outer voice chamber 16 surrounds the inner voice chamber 14 in one implementation. The voice chamber assembly including chambers 14, 16 defines an interior volume which receives the microphone assembly 17. Other arrangements may be used in other embodiments, for example, the voice chamber assembly may include only a single voice chamber or more than two voice chambers in other embodiments. In addition, the voice chamber(s) are defined by a single layer wall 42 or a wall 42 with multiple layers in different embodiments. For example, the wall 42 may be constructed with an inner stiff layer covered on both sides by a softer, sound absorbing layer.

In one embodiment, wall 42 has a total thickness of 6 mm and is comprised of a 2 mm inner layer of 80 durometer silicone rubber sandwiched between two 2 mm layers of 10 durometer silicone rubber. In another embodiment, the walls 42 which define voice chambers 14, 16 comprise relatively thick (3 to 6 mm) walls of soft, sound absorbing material, such as Sorbothane® polyurethane available from Sorbothane, Inc., or 15 durometer silicone. This also helps with isolation of the micro-phone from the speaker 20, thereby reducing audio feedback.

In one embodiment, the underwater communication system 10 includes a plurality of modules 22 which are linked together with vibration dampening connections 24, 26, such as rubber, which help to reduce or prevent feedback during operation. Connections between the modules 22 and wiring thereof are made with watertight connections and wiring in one embodiment. An outer speaking air exit port 28 including a plurality of apertures and which is in fluid communication with the outer voice chamber 16 is shown in the illustrated embodiment. Port 28 operates to exhaust air expelled by the user during speaking in one embodiment.

Different embodiments of speaker 20 which may be used in the system 10 are disclosed below and the disclosed speakers may be also be used separately from the system 10 in different implementations, for example as pool speakers where an input source such as a microphone or audio input device is above water. Some of the described speaker embodiments are efficient when submerged in water with an audio output of over 120 dBA while being relatively inefficient out of the water (e.g., 85 dBA output at a corresponding distance from the speaker).

The communication system 10 is designed to hang from a diver's BCD when not in use in one embodiment. One example of use of the underwater communications system 10 includes the diver removing their regulator from their mouth with their hand, bringing the communication system 10 to their face, pressing the face seal 12 to cover their mouth, blowing a puff of air into the face seal 12 to clear the water from the voice chambers 14, 16 (and with some example speaker embodiments—to supply air to the speaker bladder described below to expel air therefrom), sliding the power switch 32 to an "on" position, and speaking.

In some embodiments, one or more of the modules 22 of the underwater communication system 10 may be separated from one another during use. For example, the module 22 including the face seal, voice chamber(s) and microphone assembly may be manipulated by the user during use (i.e., bringing the face seal to the user's face for speaking) while the modules 22 including the circuitry 18 and speaker 20 are affixed to their dive equipment, with wires connecting the output of a pre-amplifier of the microphone assembly to a power amplifier of circuitry 18 in one embodiment described below.

Figure 2:
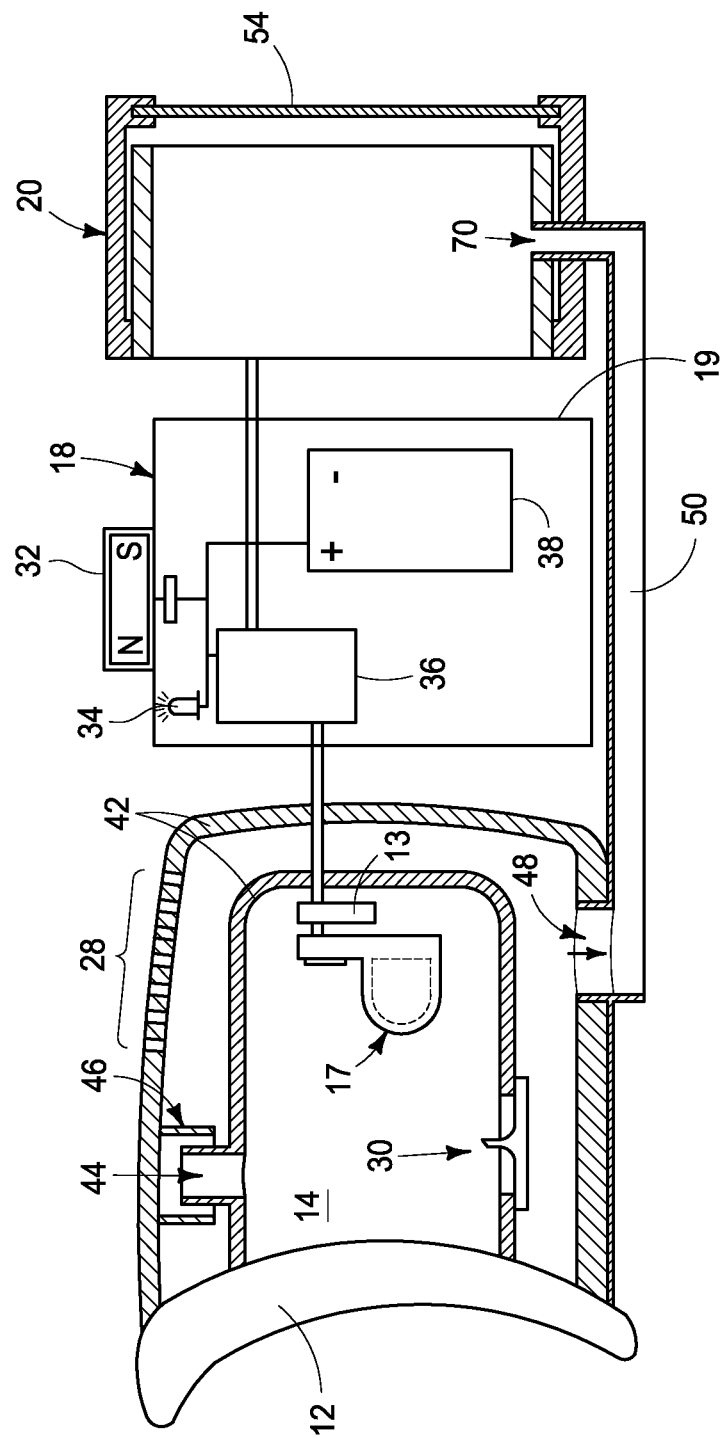
FIG. 2 is an illustrative view of internal components of an underwater communication system according to one embodiment.

Referring to FIG. 2, additional details of the embodiment of the communication system 10 of FIG. 1 are shown. The microphone assembly 17 is located within the inner voice chamber 14 and includes a microphone and also an associated pre-amplifier 13. In one embodiment, a portion of the microphone assembly 17 and pre-amplifier 13 are surrounded by a soft rubber 15 which provides additional sound dampening and assists with reduction in feedback during use.

The pre-amplifier 13 is optional and may be excluded with use of some microphones or power amplifiers. The pre-amplifier 13 may be implemented as a traditional operational amplifier which outputs a sufficient signal to the power amplifier 36 to avoid signal interference.

Circuitry 18 is contained within a sealed housing 19 and includes a power switch 32, an indicator 34 (e.g., LED) which illuminates when the communication system 10 is on, an amplifier 36 and a power source 38, such as a rechargeable battery, in the depicted embodiment. Rechargeable batteries of power source 38 may be charged by a wireless inductive charging system (e.g., Qi or Powerpad) in one arrangement.

A purge valve 30 is provided in the bottom wall between voice chambers 14, 16 in the illustrated embodiment. In some embodiments, a small chamber below purge valve 30 (e.g., within voice chamber 16) holds air during speaking which keeps water from contacting the bottom of the purge valve 30 and which provides improved isolation between the microphone assembly 17 and the speaker 20.

In one embodiment, power switch 32 is implemented as a magnet activated reed switch and mechanical relay which allows the system to be switched without the need for switch seals. Alternatively, a hall effect switch, MOSFET or other suitable switching arrangement may be used. The magnet is inside a sliding plastic piece that is elastically connected to the sealed housing 19 in one embodiment. The user slides the switch 32 including the magnet assembly towards their face to turn the unit on in one arrangement. The magnet assembly is positioned so the user naturally grabs this system 10 and naturally pushes it towards their face, which turns the system 10 on, as they press it against their face in one more specific embodiment. Other switch arrangements, such as a pushbutton, may also be used.

The microphone assembly 17 picks up sound pressure waves from the diver, converts the sound pressure waves to electrical signals which are amplified by the associated pre-amplifier 13 and applied to power amplifier 36. The pre-amplifier 13 output is the input to the power amplifier 36. The power amplifier 36 may utilize digital or analog electronic circuitry, or a combination of these two technologies and may also include noise canceling or noise mitigating circuitry.

Amplified electrical signals are applied from amplifier 36 to the underwater speaker 20 which converts the electrical signals to sound pressure waves which are transmitted thru the water to the ears of anyone and everyone within earshot (e.g., 40 ft. or more in some embodiments).

With this underwater communication system, an instructor can communicate with an entire class of students, a tour guide can talk to a large group, or an individual diver can communicate with their dive buddy or buddies, all while using conventional scuba equipment. The underwater communication system 10 can also be easily passed from one diver to another.

In one embodiment mentioned above, a user blows a puff of air into the face seal 12 when they wish to being speaking. This first puff of air clears water from the inner voice chamber 14 which flows through the purge valve 30 into the outer voice chamber 16 and exits the system 10 via a water and air exit port 48 which has a diameter of approximately ½" in one embodiment. Accordingly, voice chambers 14, 16 are filled with air during use.

As a puff is more air than required to clear the inner voice chamber 14, the extra air exits through the purge valve 30 as well as an inner speaking air exit port 44 and fills the outer voice chamber 16 and exits the system 10 via air exit port 28. The purge valve 30 is then sealed off to reduce the transmission of sound from the speaker 20 to the microphone, reducing feedback. The diver maintains a seal with the face seal during the evacuation of water from the voice chambers 14, 16 and then can begin to speak.

As discussed below, the air introduced by the diver may also be passed to the speaker 20 in some embodiments to evacuate or expel water from the speaker 20 prior to use and to increase the efficiency of the speaker 20.

The inner speaking air exit port 44 is a small diameter tube (e.g., inside diameter of approximately ¼") in one implementation as the flow rate of air exhaled by the user is low when speaking. When the user speaks into the communication system 10, the air from speaking exits thru the inner speaking air exit port 44 while the purge valve 30 remains sealed. The exhaled air passes around baffle 46 and continues out thru the outer speaking air exit port 28 in one implementation. Baffle 46 blocks some external sounds from entering the inner voice chamber 14 in one implementation.

Apart from allowing the air from the diver to exit the communication system 10, the outer speaking air exit port 28 also functions as a bubble silencer in one implementation. In particular, when a person speaks, they are exhaling air at a very low rate. When air is exhaled from a regulator, the air forms large bubbles that are very loud. They are very annoying when they flow close to the diver's ears and they seem to produce low frequency sound. If the air bubbles are broken down into smaller bubbles, they are much, much quieter, producing a "sssshhhh" sound. Some embodiments of the port 28 of communication system 10 operates as a specially designed bubble silencer to break the air exiting during speaking into small bubbles.

In some embodiments, a simple screen or sponge may be used for port 28. Alternatively, a grid of small holes or apertures may be used for the port 28 and which may provide additional silencing of the bubbles compared with use of a screen or sponge. Air flowing thru a screen or sponge breaks some of the air into small bubbles, but as most of them are almost touching, they immediately begin to join together to form larger bubbles, making a lot of noise. One example is a grid of small holes or apertures with consistent spacing between holes. With enough space between the holes, the bubbles do not connect until well above the diver. The hole centers may be equidistant from their immediate neighbors in one embodiment for increased efficiency (most air flow in the least area). The holes are the vertices of interconnected equilateral triangles in one embodiment. Bubble size is dependent on the hole size and flow rate, and the bubbles are always larger than the hole size. Accordingly, the separation distance utilized depends on the hole size in one embodiment.

In one embodiment, the bubble silencer utilizes holes which have a diameter less than the spacing of the holes from one another, and may be provided in a ratio of hole spacing to hole diameter of at least 8:1. In a more specific embodiment, the outer speaking air exit port may be a 1 mm thick PTFE panel with 75 holes each of 0.6 mm diameter equidistantly spaced 5 mm apart in one embodiment. It is desired to maintain the bubble silencer in a substantially horizontal position during speaking as shown in FIGS. 1 and 2 in one embodiment.

As mentioned above, the water and air exit port 48 allows water (as well as any excess air from the first puff) to exit out of the communication system 10 through the bottom of the outer voice chamber 16. The water and air exit port 48 may also feed air via an air passage 50 to interior chambers of the speaker 20 as described in some embodiments below. In one embodiment, the communication system 10 is positioned as shown in FIGS. 1 and 2 during use where the air passage 50 is at the bottom the system 10.

In one embodiment, air passage 50 is implemented as an elongated channel which is open at the bottom to allow air to flow between port 48 and speaker 20 while water may exit the bottom of the passage 50.

The discussion proceeds with respect to details of various embodiments of underwater speakers 20a-20f which may be used to output sound pressure waves of audible content underwater. Some embodiments of the underwater speakers have similarities in design and construction and may radiate sound in different patterns, for example including a dipole pattern and a cardioid pattern in some examples described below.

As discussed below, some embodiments of the underwater speaker 20a-20f are constructed with a housing, a tactile transducer or exciter (referred to hereafter as an exciter including a moving voice coil and magnet structure) a rigid lightweight transducer member, a mounting plate situated inside the housing to mount the exciter, and a flexible rubber surround. In these example embodiments, the exciter and transducer member convert electrical signals to sound pressure waves which are emitted into the water adjacent to the submerged underwater communication device.

The exciter is mounted to a flat, rigid surface, such as the transducer member as described below. As discussed below in some embodiments, a suspension system such as a support spider may be used to keep the moving voice coil which is attached to the transducer member centered in the magnetic gap. The exciter moves the transducer member to generate sound in the water in response to signals from the power amplifier 36. Exciters are more rugged for use underwater as well as producing sound underwater with increased efficiency compared with traditional paper/polymer cone/foam surround speakers.

The flexible rubber surround loosely connects the transducer member to the housing and seals water out of internal space of the speaker in some embodiments. The transducer member forms the boundary between the sealed internal speaker volume (the inside) and outside (the water/marine environment) of the speaker in some embodiments. A feature of the transducer member in these embodiments is that it can be as large as the diameter of the Housing which provides high efficiency in transferring sound energy to the water while being compact. In addition, both sides of the transducer member may be exposed to water in some of the arrangements disclosed below.

Referring to FIGS. 3A-3D, one embodiment of the underwater speaker 20a is shown. Underwater speaker 20A includes a cylindrical housing 51, surround 52, transducer member 54, opening 56, end wall 58, a bladder 60, a tactile exciter 62 (e.g., exciter body/magnet 64 and moveable exciter voice coil 66) and a mounting plate 68.

Figure 3C:
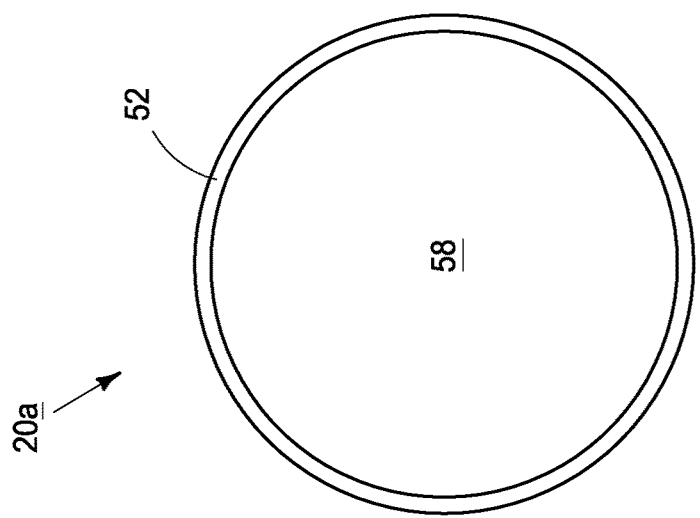
FIG. 3C is a rear view of the speaker assembly according to the first embodiment.
Figure 3B:
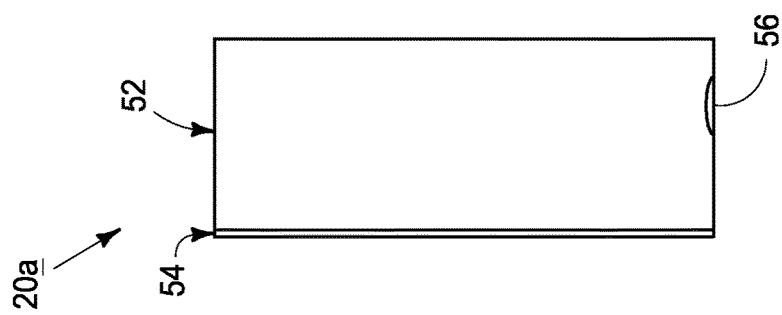
FIG. 3B is a side view of the speaker assembly according to the first embodiment.
Figure 3A:
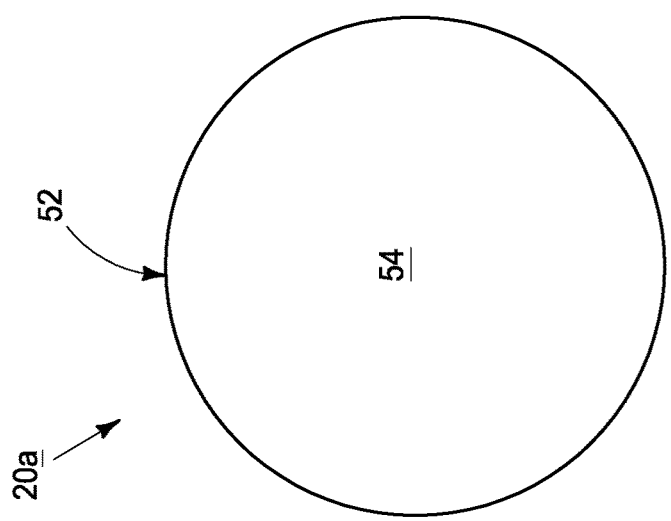
FIG. 3A is a front view of a speaker assembly according to a first speaker embodiment.
Figure 3D:
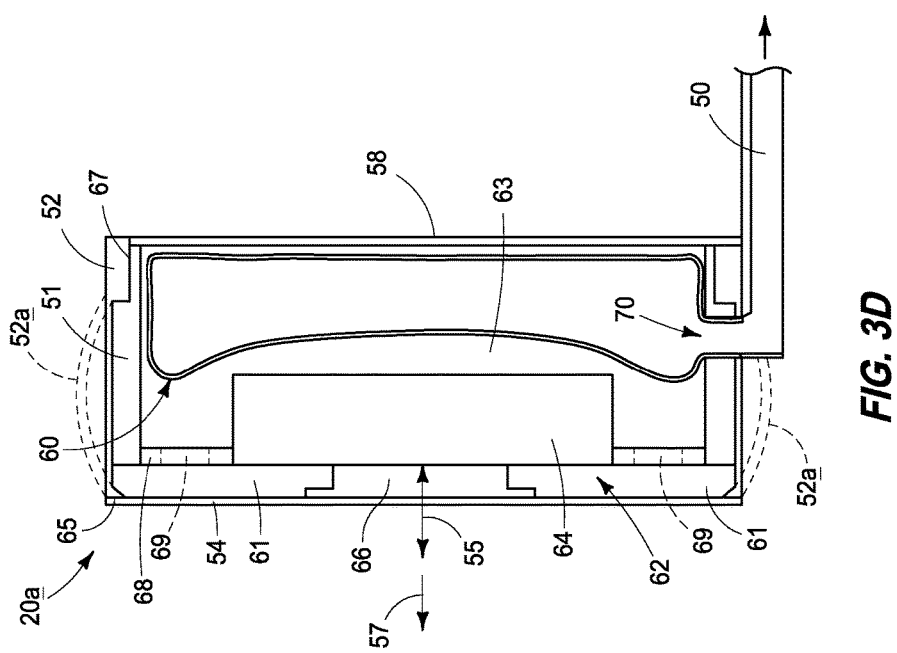
FIG. 3D is a sectional view of the speaker assembly according to the first embodiment.

Electrical wires from the power amplifier 36 (not shown in FIG. 3D) provide the amplified signals to the voice coil 66 which causes the voice coil 66 to move 55 left and right within the exciter body/magnet 64 and to move transducer member 54 in FIG. 3D which results in the emission of sound pressure waves 57 from the front of the underwater speaker 20a. The front end of the speaker 20a is the left side and the back end of the speaker 20a is the right side in FIG. 3D. Transducer member 54 of the underwater speaker 20 moves to generate sound pressure waves of content which are audible to humans (e.g., voice, music, etc.) and are emitted into the surrounding water as discussed in additional detail below.

In one embodiment, transducer member 54 is a thin flat plate (e.g., 1/16" thick aluminum) having an area less than 1 square foot. Other materials may be used, such as carbon fiber, in other implementations.

The left surface of the transducer member 54 shown in FIG. 3D is exposed to and contacts the body of water when the speaker 20a is submerged. When vibrated by the voice coil 66 of exciter 62, the transducer member 54 generates sound pressure waves in the body of water which radiate outward from the speaker 20a.

In this disclosed embodiment, a pressure control system is configured to vary the pressures applied to the right surface of the transducer member 54 corresponding to different depths of submersion of the speaker 20a and corresponding different pressures exerted by the body of water. In one embodiment, the pressure control system varies the pressures applied to the right surface of the transducer member 54 to substantially balance the static pressure on the right surface to substantially equal the static pressure applied to the left surface of the transducer member 54 by the body of water.

In one embodiment, the pressure control system is implemented as a bladder 60. The bladder 60 is thin collapsible flexible silicone rubber (e.g., 40 durometer and 0.5-1 mm thick) and is located in the housing 51 which is PVC (or other suitable material) and away from the transducer member 54 in one embodiment.

Outer edges of the transducer member 54 are attached via a flexible surround 52 to housing 51 in some embodiments. The inside of the speaker 20a is sealed by transducer member 54, housing 51, surround 52 and end wall 58 to from an inner chamber which includes the volume of the bladder 60 and the remaining volume includes fixed dry air the inside of the speaker 20a is isolated from the body of water.

According to one embodiment, when the speaker 20a is assembled (e.g., assembly at or near sea level), the bladder 60 is totally collapsed and the remainder of the inside volume of the speaker 20a is filled with fixed dry air. The inside of the speaker 20a is then sealed off and the fixed dry air is now a finite number of air molecules within the inside of the speaker 20a. The volume of the inside of the speaker 20a is occupied by either the fixed dry air or the bladder 60.

The bladder 60 has an opening 70 is at the bottom of the speaker 20a which is in fluid communication with the water and air exit port 48 and air passage 50 to allow water to freely move in and out of the bladder 60. As mentioned above, the bladder 60 of the presently described embodiment functions as a first configuration of a pressure control system which provides different pressures behind the transducer member 54 in an effort to substantially provide pressure equilibrium upon the opposing surfaces of the transducer member 54 at different submerged depths. The pressure control system operates to provide static pressures on the inside surface of the transducer member 54 which are substantially balanced (e.g., pressure difference of less than 0.2 psi in one embodiment) with the static pressures on the outside surface of the transducer member 54 and which increase as the system 10 is submerged into increasing depths in the body of water.

For example, the bladder 60 has different volumes corresponding to different depths of submersion of the communication system 10. The fixed dry air contracts in volume as pressure increases or temperature decreases, or expands if pressure decreases or temperature increases. The mounting plate 68 has openings 69 so that fixed dry air can freely move back and forth thru the mounting plate 68 between chambers 61, 63.

The example pressure control system imparts increasing pressure to the internal surface of the transducer member 54 as the speaker 20 is submerged to increasing depths of the body of water. In the described embodiment, the bladder 60 either inflates or deflates with water during submersion to occupy the space not occupied by the fixed dry air.

During use, the ambient pressure upon the speaker 20a increases as the diver descends into the body of water and water enters the bladder 60 thru the opening 70 because the fixed dry air is compressed, and therefore the volume of fixed dry air is reduced. Thus, equal pressure is maintained on the front and back sides of the transducer member 54 as the system 10 submerges. In particular, the pressure increases on the back surface of the transducer member 54 as the diver descends deeper while the front surface of the member 54 which is directly exposed to the water is also subjected to the increasing pressures.

For example, at the surface of the water, the bladder 60 is nearly totally collapsed and the remainder of the volume of the inside space of the speaker is occupied by the fixed dry air. FIG. 3D represents the speaker submerged to a depth of approximately 60 feet. At deeper depths, the bladder 60 expands more, and the fixed dry air is compressed more.

When speaker 20a is submerged, water fills the bladder 60 via the air passage 50 as mentioned above. However, the speaker 20a of FIG. 3D works with improved efficiency (louder) if the full air space behind the transducer member 54 is restored to the approximate volume at the surface. This is accomplished in one embodiment by holding the speaker 20a in the normal use position where the passage 50 is the low point of the speaker 20a and venting the diver's exhaled air from the voice chamber 16 into the bladder via the passage 50. As air is introduced to the bladder opening 70 (at the bottom of the speaker housing) the air enters the bladder 60 and expels or displaces the water therein out the opening 70 and out of channel 50 into the body of water. The volume of air space on the back side of the transducer member 54 is now increased which increases the efficiency of speaker 20a.

For applications of speaker 20a other than the diving (e.g., pool speakers connected to a microphone and/or a separate source of audio, such as MP3s or CDs for example), air can be introduced into the bladder 60 to displace water therein from an air filled container, pressurized line from the surface, or other source once the speaker reaches the desired depth.

In one embodiment, it is desirable to keep the fixed dry air at a specified volume at the start of a dive. The volume of the fixed dry air should be such that the bladder 60 is nearly totally collapsed and the position of the voice coil of the exciter is at its neutral point before entering the water in one embodiment. The fixed dry air has a minimum and a maximum volume. The minimum volume of the fixed dry air is the volume that surrounds the exciter 62 that cannot be filled by the bladder in one example. If the volume moves out of this range, damage to or malfunction of the exciter 62 may occur due to the ambient pressure trying to move the transducer member 54 inward or outward beyond its designed range.

The fixed dry air may expand at low pressure (such as in an aircraft) or at high temperature to a volume greater than the available inside volume which may result in damage to the exciter. Rather than have the user adjust the quantity of fixed dry air, a method to compensate for this issue is to utilize a surround 52 which may deform (e.g., stretch) and which has elongated sides over sides of the housing 51 as shown in FIG. 3D. Surround 52 is a flexible rubber in one implementation. The expanded elongated sides are shown by reference 52a in FIG. 3D to create additional volume inside of the speaker 20a for the fixed dry air without displacing the transducer member 54 more than its maximum length of travel to avoid damage to the exciter 62 in one example embodiment. Under normal conditions, the elongated sides of the surround 52 are in contact with the housing 52 and the volume of the fixed dry air volume at normal conditions would be the same as if this design feature of the surround 52 was not there, and the size of the speaker 20a is minimized. Speakers 20a for deeper depth limits can be designed by including additional inside space and a correspondingly larger bladder 70. In one embodiment, surround 52 is adhered to transducer member 54 by a first glue point or bond 65 and to housing 51 via a second glue point or bond 67 which permit expansion to create the additional volume inside speaker 20a described above.

Figure 4A:
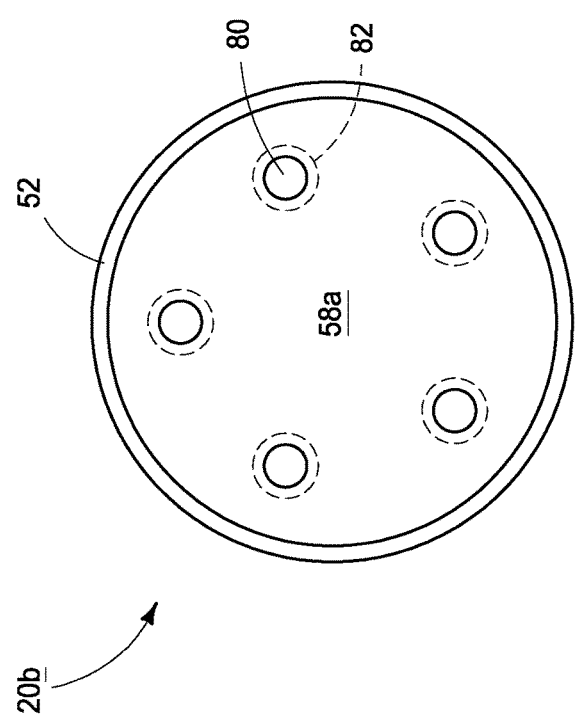
FIG. 4A is a rear view of a speaker assembly according to a second embodiment.
Figure 4C:
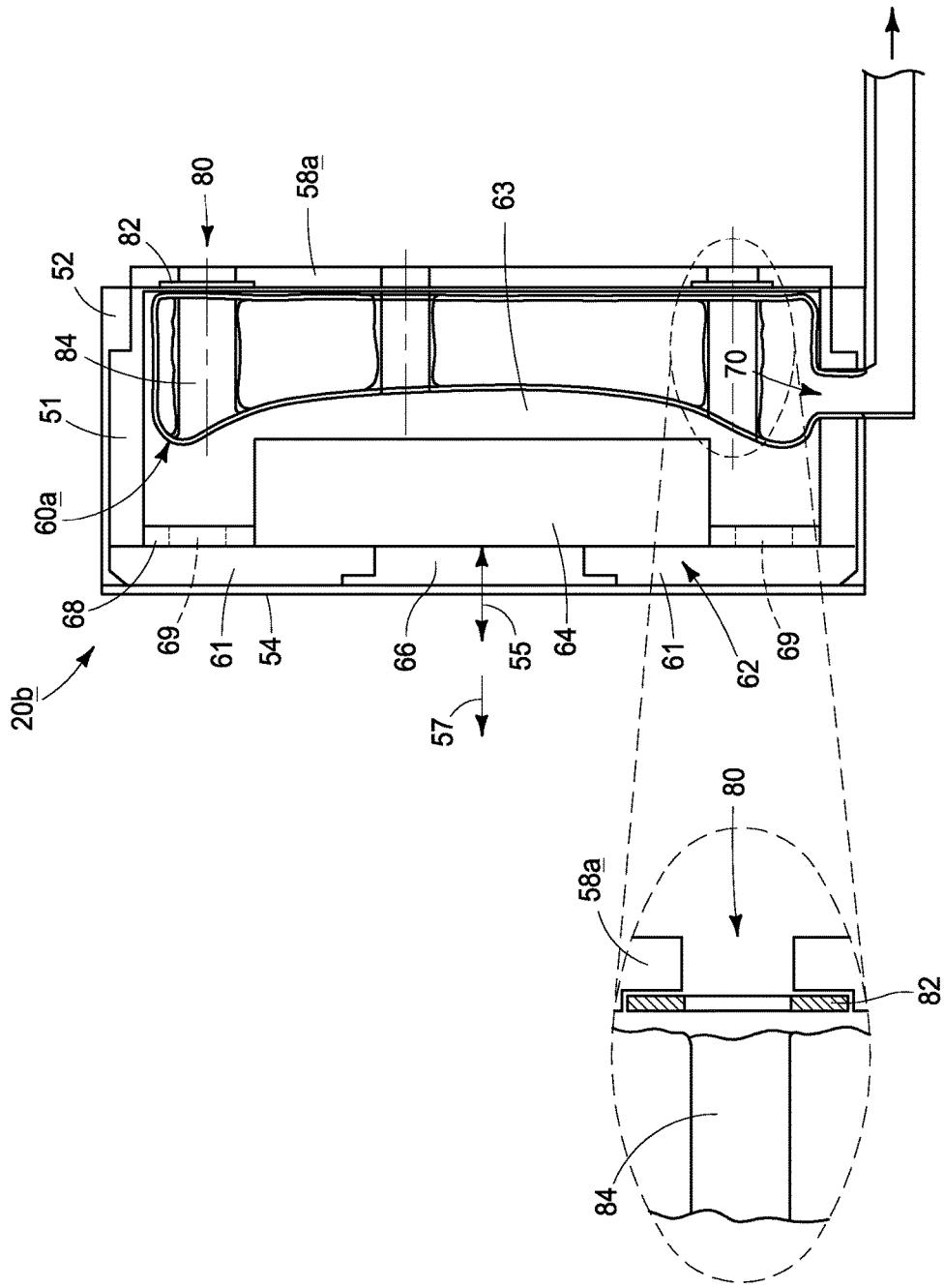
FIG. 4C is a sectional view of the speaker assembly according to the second embodiment.

Referring to FIGS. 4A-4C, another embodiment of an underwater speaker 20b is shown which is similar to the speaker 20a discussed above. Speaker 20b is similar to speaker 20a with the addition of one or more acoustic ports 80 (the depicted example embodiment includes five acoustic ports 80). The front end of the speaker 20b is the same as the front end of the speaker 20a shown in FIG. 3A and is not shown.

The acoustic ports 80 are apertures which pass through bladder 60a and are individually sealed by a respective acoustic membrane or vent 82 to prevent water from entering the ports 80 and maintain the fixed dry air inside the speaker 20b as shown in FIG. 4C. Acoustic vents 82 are individually a 0.3 mm thick silicone rubber disk which seals individual acoustic ports 80 which are 10 mm in diameter in the described embodiment.

The bladder 60a in this design has an air passage 84 for each acoustic port 80. Air passages 84 are thru-holes that penetrate the air bladder 60a allowing the fixed dry air inside the speaker 20a to contact the acoustic vents 82. This allows sound pressure waves generated from the transducer member 54 within the inside of the speaker 20b to radiate directly to the acoustic ports 82 without interference from the bladder 60a and out the back of the speaker 20a.

This sound energy passing through the acoustic ports 84 is 180 degrees out of phase with the sound energy radiating from the front of the speaker 20b (i.e., sound energy radiating from the transducer member 54 directly into the water). This creates a cardioid sound radiation pattern for the speaker. By adjusting the number, size and placement of the acoustic ports 80, the sound energy transmitted behind the speaker 20B can be adjusted. By adjusting this sound energy, the radiation pattern of the speaker 20b can be adjusted to create a null space where there is little or no sound energy behind the speaker 20b to locate the microphone assembly which reduces or eliminates audio feedback of the system is eliminated. For example, referring again to FIG. 1, the acoustic ports 80 may be configured and positioned in one embodiment such that a null space of sound energy is provided at the location of the microphone assembly to reduce interference. This is discussed in additional detail with respect to FIG. 9 below.

Figure 5B:
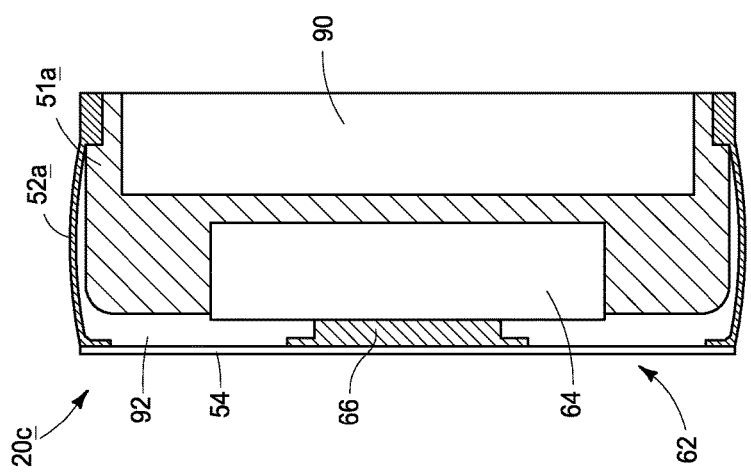
FIG. 5B is a sectional view of the speaker assembly according to the third embodiment.

Referring to FIGS. 5A-5B, another embodiment of an underwater speaker 20c is shown. The front end of the speaker 20c is the same as the front end of the speaker 20a shown in FIG. 3A and is not shown. In this embodiment, the end wall is omitted and housing 51a includes a recess 90.

In addition, a low density, low viscosity, very low compressibility (or incompressible) fluid 92 is provided behind the transducer member 54. In some embodiments, fluid 92 has a low mass and includes a mixture of glass microspheres in low viscosity polydimethylsiloxane or glass microspheres mixed with molybdenum disulfide powder and air. Other examples of fluid 92 which may be used include mineral oil or silicone. During sound generation, transducer member 54 moves inward and outward which displaces the fluid 92.

As shown, the surround 52a extends the length of the housing 51a and is illustrated at an expanded position away from the side wall of housing 51a. Surround 52a is configured in this embodiment to move between a static position where the surround contacts the sidewall of the housing 51a to the expanded position shown. In particular, as the transducer member 54 moves inward (i.e., to the right in FIG. 5B) during operation, the surround 52a flexes radially outward, and the fluid 92 moves easily with minimal volume of fluid movement from the area behind the transducer member 54 to the space between the sidewall of the housing 51a and the expanded surround 52a. The surround 52a is additionally configured such that, when the transducer member 54 moves outward, the fluid 92 returns to the space behind the transducer member 54 with minimal volume of fluid movement.

In particular, as the movement of fluid consumes energy, minimizing movement of fluid 92 conserves energy, and an increased amount of energy produces a higher amplitude and higher fidelity sound. A perfect fluid 92 would have no mass, no viscosity and be incompressible. The closer to perfect the fluid 92 is, the more efficient the speaker 20c operates, as more energy can be transferred outside into the water via the transducer member 54.

Figure 6:
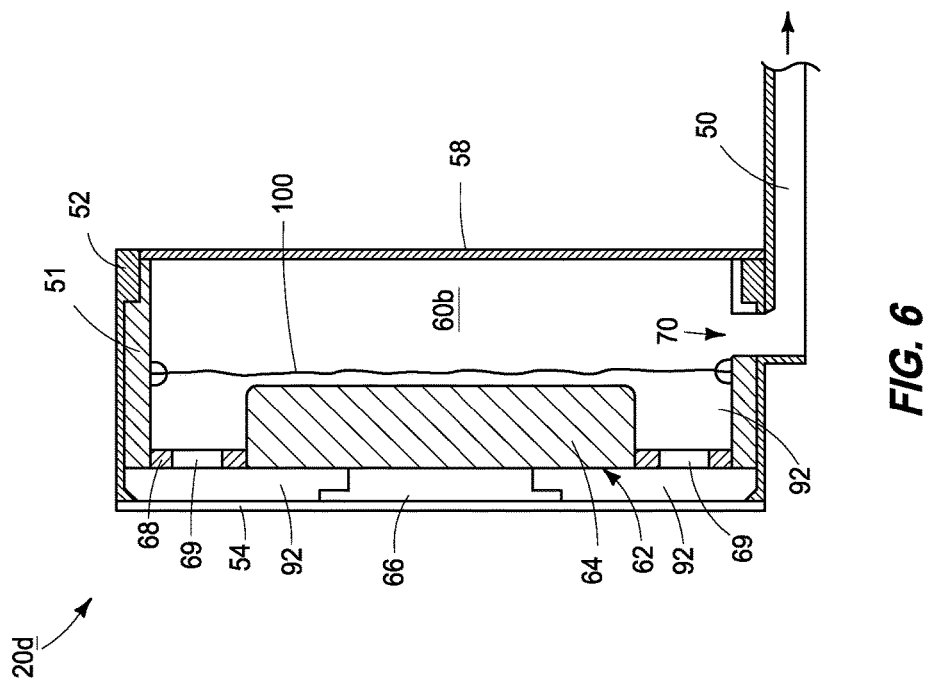
FIG. 6 is a sectional view of the speaker assembly according to a fourth embodiment.

Referring to FIG. 6, another embodiment of an underwater speaker 20d is shown. The front end of the speaker 20d is the same as the front end of the speaker 20a shown in FIG. 3A and is not shown. The back end of speaker 20d is similar to the back end of speaker 20a shown in FIG. 3C and is not shown.

This embodiment of speaker 20d includes features of the embodiments of speakers 20a, 20c discussed above. In particular, the inside of speaker 20d includes fluid 92 on both sides of the mounting plate 68 as well as a bladder 60b defined by end wall 58 and a thin, flexible membrane or barrier 100, such as 1 mm thick 40 durometer silicone rubber, which is sealed or bonded to the sidewall of the housing 51. The bladder 60b in this embodiment may or may not be configured to fully collapse and is inflated to fill as much of the inside of the speaker 20d as practical with the balance of the inside being filled with the fluid 92 in one embodiment. Barrier 100 partitions the inside of speaker 20d into a fluid side (i.e., to the left of barrier 100 in FIG. 6) and a wet air chamber (i.e., to the right of barrier 100 in FIG. 6) in one implementation.

The fluid 92 is in direct in contact with the transducer member 54 and surrounds the exciter 62 in one embodiment. To achieve increased efficiency, the amount of fluid 92 is minimized to allow bladder 60b to occupy as much space inside the speaker 20d as practical. If the fluid used is totally incompressible, the bladder 60b is displaced by the movement of the fluid 92 caused by the movement of the transducer member 54. If the fluid is somewhat compressible, the bladder 60b expands to fill an increased volume within the inside of the speaker 20d when at high ambient pressures (i.e., deep in the water column), and shrinks when at lower ambient pressures (on the surface or at higher altitudes, such as on a high altitude aircraft).

In one embodiment, the bladder 60b has an opening 70 at the bottom which is coupled with air passage 50 and voice chamber 16 and is open to allow water to freely move in and out of the bladder 60b as described with respect to speaker 20a above and shown in FIGS. 3A-3D. Bladder 60b at least partially fills with water when submerged below the water. The bladder 60b is filled with air replacing the water by directing an initial puff of air from the user as well as exhaust air during speaking from the voice chamber 16 via the air passage 50 to bladder 60b in one embodiment which improves the efficiency of speaker 20d when using a less than perfect fluid 92.

Referring to FIGS. 7A and 7B, another embodiment of an underwater speaker 20e is shown. Speaker 20e is a dipole speaker design where both the front and back of the transducer member 54 are in contact with water. Speaker 20e transmits sound pressure waves into the water in both directions which are 180 degrees out of phase from one another in this example embodiment.

Exciter 62 is provided within a chamber which is enclosed by a thin, flexible rubber enclosure 110 in the illustrated embodiment. The enclosure 110 protects the exciter 62 from contact with the water and may be filled with air or fluid 92, which is the same as the fluid discussed above with respect to speakers 20c, 20d in one embodiment. The exciter enclosure 110 is attached or bonded to the center of the transducer member 54 and moves with transducer member 54 in this embodiment.

In addition, a flexible surround 52b, such as rubber, may or may not be used to attach transducer member 54 to the housing 51b. Housing 51b enhances audio quality and serves to protect the transducer member 34 from accidental contact and may be a short cylinder or rigid wire cage in example implementations.

A rigid support spider 112, such as PVC or stainless steel, is used to attach the exciter 62 and enclosure 110 to the housing 51b. Spider 112 includes a plurality of arms 114 attached to housing 51b and a support ring 116 which supports exciter enclosure 110.

Speaker 20e radiates sound pressure waves both forward and backward. The interference of these waves causes zones where the sound is cancelled. The microphone assembly 17 may be located in one "cancelled zone" (i.e., a defined distance from the transducer member 54 where the sound pressure waves cancel) in one implementation which reduces or eliminates audio feedback. This is described in additional detail with respect to FIG. 10 below. In another embodiment, sound pressure waves are only emitted in one direction.

Figure 8B:
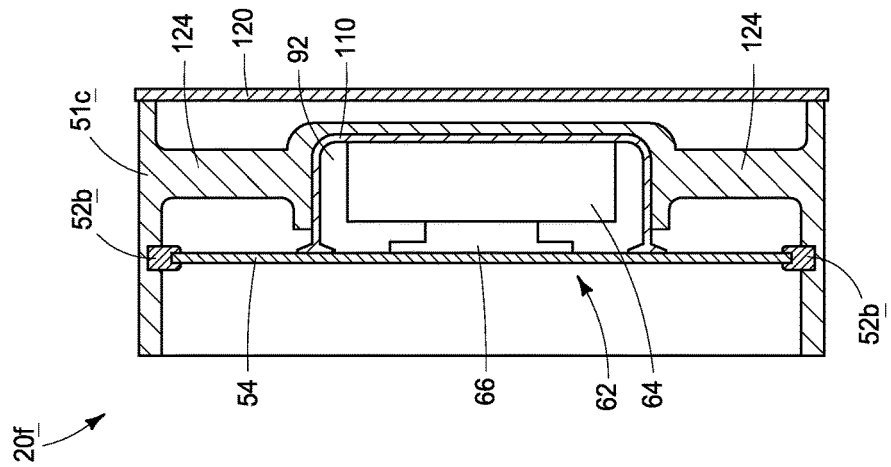
FIG. 8B is a sectional view of the speaker assembly according to the sixth embodiment.
Figure 8A:
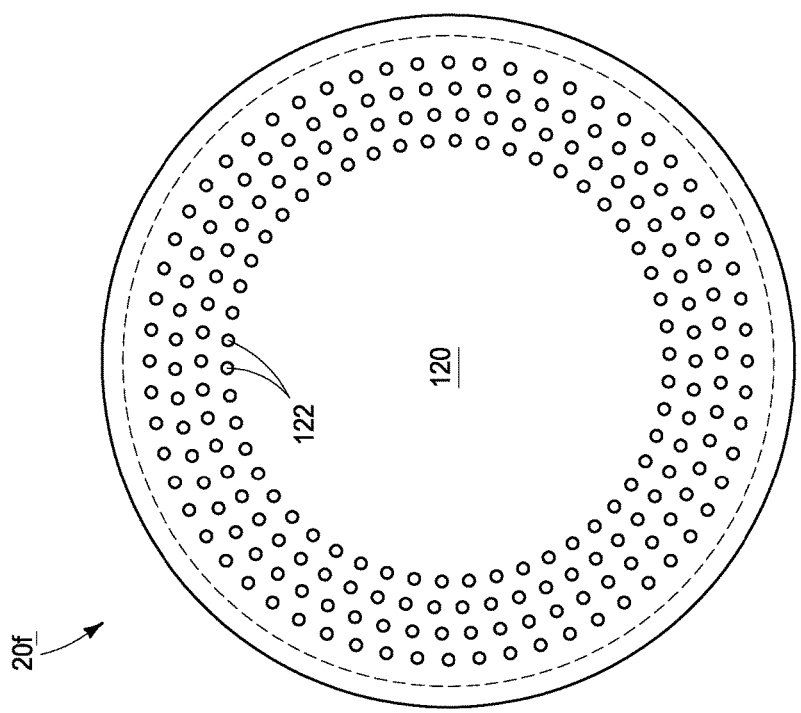
FIG. 8A is a rear view of a speaker assembly according to a sixth embodiment.

Referring to FIGS. 8A and 8B, another embodiment of an underwater speaker 20f is shown. Speaker 20f is a cardioid speaker design and both the front and back of the transducer member 54 are in contact with water. Speaker 20f transmits sound pressure waves into the water in both directions which are 180 degrees out of phase in this example embodiment. In another embodiment, sound pressure waves are only emitted in one direction.

Speaker 20f radiates sound in a cardioid pattern with maximum sound pressure directly in front of (i.e., to the left in FIG. 8B) and perpendicular to the transducer member 54 and the sound pressure is lower to the right of the speaker 20f in FIG. 8B due to a perforated restrictor plate 120 at the back of the speaker 20f. Microphone assembly 17 may be located to the right of the speaker 20f within a cancelled zone in order to reduce or eliminate feedback in one embodiment.

Restrictor plate 120 is rigid rubber and has a plurality of holes 122 (e.g., $1/16^{th}$) to restrict the sound pressure in the backward or rearward direction in one implementation. As mentioned above, this sound pressure is 180 degrees out of phase with the sound pressure wave radiating out the front of the speaker 20f. Together, the sound pressure out the front and the rear of the speaker 20f combine to create a cardioid radiation pattern. The holes or perforations in the restrictor plate 120 may be adjusted to alter the cardioid pattern to best suit the communication system in one embodiment. For example, in other embodiments, fewer numbers of holes are used each having increased diameters (e.g., eight ¼" holes).

In the illustrated embodiment, the housing 51c has a plurality of support ribs 124 (e.g., 2, 3, 4 or more) which rigidly hold the exciter body 64 and result in improved transfer of energy from the exciter 62 to the transducer member 54. The back of the exciter body 64 is bonded to the housing 51c (with enclosure 110 therebetween) while the sides of enclosure 110 are not bonded or attached to support ribs 124 in one embodiment. Water is provided to both sides of transducer member 54 via the opening at the front of the speaker 20f and the openings 122 at the back of the speaker 20f and between the support ribs 124.

Figure 9:
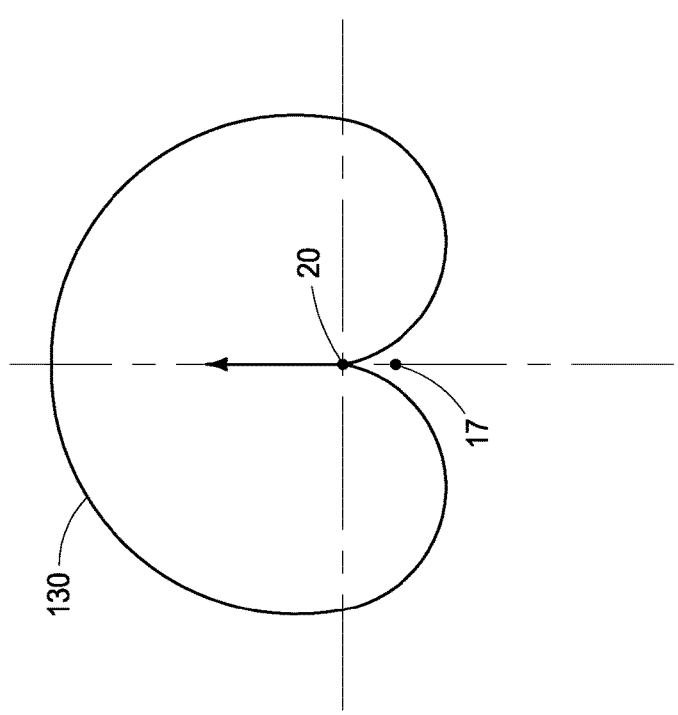
FIG. 9 is an illustrative representation of a cardioid radiation pattern according to one embodiment.

Referring to FIG. 9, a cardioid radiation pattern 130 of emitted sound pressure waves is shown. A speaker 20 having a cardioid radiation pattern 130 (e.g., speaker 20b shown in FIGS. 4A-4C and speaker 20f shown in FIGS. 8A and 8B) is positioned at the center of the pattern 130 and is pointing in the upward direction in FIG. 9. The farther the pattern 130 is away from the speaker 20 in a direction indicates increased sound energy in that direction. As shown and described above in some embodiments, microphone assembly 17 may be positioned in a null area to the rear of the speaker 20 and outside of radiation pattern 130 which results in reduced feedback.

Figure 10:
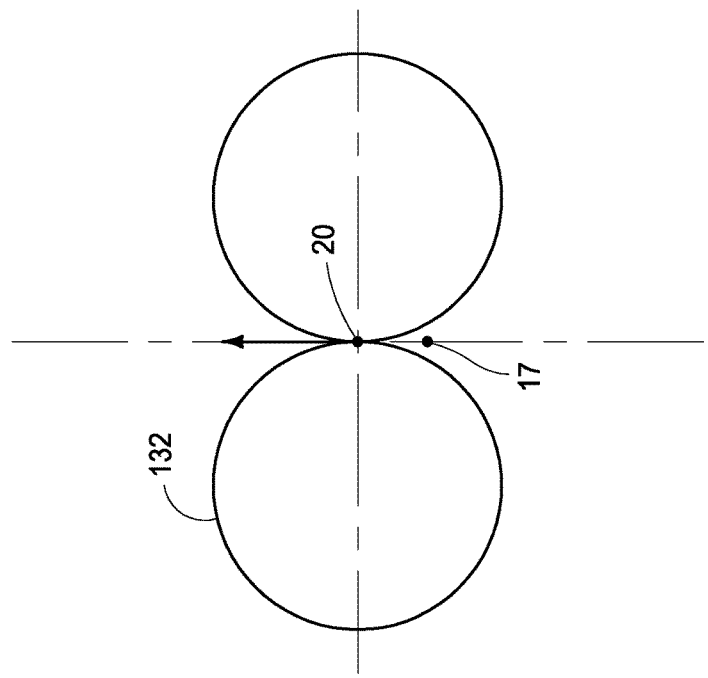
FIG. 10 is an illustrative representation of a dipole radiation pattern according to one embodiment.

Referring to FIG. 10, a dipole radiation pattern 132 of emitted sound pressure waves is shown. A front of a speaker 20 having a dipole radiation pattern 130 (e.g., speaker 203 shown in FIGS. 7A and 7B) is pointing in the upward direction in FIG. 10. Similar to FIG. 9, microphone assembly 17 may be positioned in a null area to the rear of the speaker 20 and outside of radiation pattern 132 in some embodiments which results in reduced feedback.

Referring to FIGS. 11A-11F, one example embodiment of a microphone assembly 17 is shown. The illustrated microphone assembly 17 includes a body 140, a microphone capsule 142, a collapsible air chamber 144, and an acoustic membrane 146 which operates as a vent. The example microphone assembly 17 of FIGS. 11A-11E produces good fidelity output and is very rugged.

As discussed below, collapsible air chamber 144 operates as a pressure control system which is configured to apply different pressures to the acoustic membrane 146 which correspond to different depths of the underwater microphone assembly within the body of water.

Body 140 is a sealed housing which seals microphone capsule 142 from the environment within the voice chamber 14. Microphone capsule 142 is commercially available and a Knowles BJ-21590 capsule having a small size (4×6×8 mm) and a frequency response of ~500 Hz to 5 kHz which is adequate for voice transmission is used in one embodiment. This frequency response range eliminates the need to filter out the low and high frequencies which may be a problem due to the geometry of the communication system 10 as speaking into a very small volume produces high amplitude low frequencies, while noises from bubbles and other sources produce unwanted high frequencies. A plurality of wires 154 provide the output of the microphone to a pre-amplifier or amplifier in one embodiment.

As described further below, an airway 148 operates as an input airway which provides fluid communication between the microphone 143 of the microphone capsule 142 and the exterior of the body 140. In particular, input airway 148 allows sound pressure waves within voice chamber 14 to reach the microphone 143 in the described embodiment.

Acoustic membrane 146 is located between the internal volume of voice chamber 14 and the input airway 148 and in one embodiment. Membrane 146 operates as an acoustic vent and is semi-permeable and allows air molecules and sound pressure waves in voice chamber 14 to pass freely, but is impervious to water and blocks water within voice chamber 14 from damaging microphone capsule 142 in one embodiment. Membrane 146 and adhesive ring 160 are the components of commercially available products (e.g., a GAW325 series vent that is constructed from ePTFE material and available from W.L. Gore & Associates, Inc. may be used in one embodiment). This membrane 146 acts to pass sound pressure waves generated by the user (voice) which are present in the voice chamber 14 into the microphone capsule 142. The sound pressure waves are directed by the input airway 148 to microphone 143 of microphone capsule 142 which generates electrical signals which correspond to the received sound pressure waves.

As discussed below, an additional airway 150 which operates as a pressure equalization vent may also be provided in some embodiments. Airway 150 is in fluid communication with voice chamber 14 and interior volume 168 which is connected via airway 149 to airway 148 and to the microphone 143 of microphone capsule 142. In addition, airways 148, 150 are also in fluid communication with collapsible air chamber 144. A semi-permeable membrane 152 is provided to prevent passage of water from voice chamber 14 to microphone capsule 142 via airway 150. Membrane 152 and adhesive ring 160 are the components of a PE7 series vent available from W.L. Gore & Associates, Inc. in one embodiment. In addition, an airway 149 is shown in FIGS. 11C and 11F which connects the interior volume 168 of the chamber 144 with airway 148 and capsule 142.

Figure 11F:
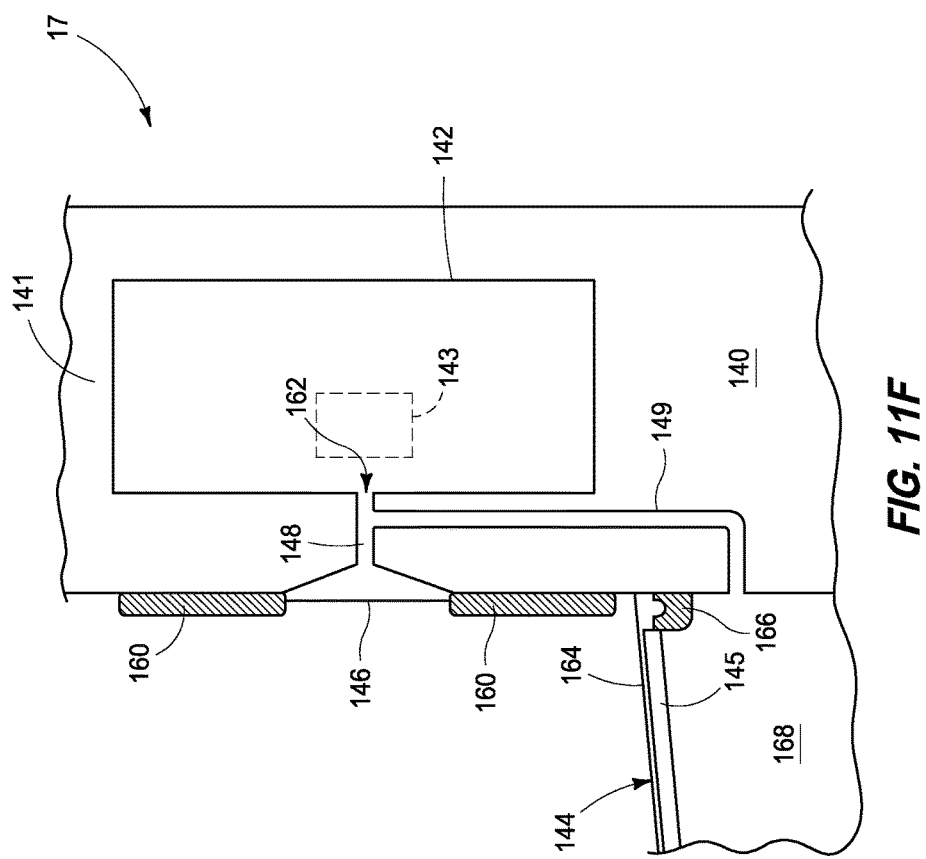
FIG. 11F is a cross-sectional view of a body of the microphone assembly according to a first embodiment.

Referring to FIG. 11F, additional details of microphone assembly 17 according to one embodiment are shown. An adhesive ring 160 is used to adhere the acoustic membrane 146 to body 140 in a manner which prevents water from entering airway 148 and membrane 146 functions as an acoustic vent which passes sound pressure waves within voice chamber 14 to airway 148. Airway 148 directs the sound pressure waves received through the acoustic membrane 146 through a housing 141 of body 140 to an input port 162 and microphone 143 of microphone capsule 142 which converts the sound pressure waves into corresponding electrical signals.

Airway 149 provides fluid communication of the interior volume 168 of chamber 144 with airway 148 and operates to reduce or minimize pressure differentials across the membrane 146. Also, airway 150 connects one side of membrane 152 with interior volume 168 and also operates to reduce or minimize pressure differentials across membrane 152. The pressure control system including the chamber 144 operates to provide static pressures to the interior surfaces of membranes 146, 152 (i.e., the surfaces adjacent to airways 148, 150) which are substantially balanced with the static pressures which are exposed to the exterior surfaces of the membranes 146, 152 (i.e., the surfaces adjacent to voice chamber 14) at different depths of submersion of the microphone assembly 17 in the body of water. In one embodiment, pressure differences between the surfaces of the membranes 146, 152 are maintained to be less than 0.1 psi.

A seal 166 joins the chamber 144 to the body 140 in a watertight manner in the illustrated embodiment. A microphone 143 of microphone capsule 142 receives sound pressure waves from port 162 and generates electrical signals corresponding to the received sound pressure waves and which may be amplified and applied to speaker 20 in one embodiment.

In one embodiment, microphone assembly 17 includes a microphone fixed volume space (e.g., a volume of 150 to 200 cubic millimeters) which includes the volumes of the space that is inside the microphone assembly 17 not including the collapsible air chamber 144 and which are in fluid communication with one another. For example, the microphone fixed volume space includes volumes of air between each of the membranes 146, 152 and microphone capsule 142 and collapsible air chamber 144, inside microphone capsule 142, and airways 148, 149, 150.

Membranes 146, 152 act as pressure equalization vents in one embodiment. In particular, it is desired to maintain substantially equal pressures on both sides of membranes 146, 152 since some membranes 146, 152 are only rated to withstand pressure differentials of about 1 atm to avoid breakage, but may be permanently stretched if subjected to lesser pressure differentials. Although they do not allow water to pass at these pressures, they do stretch with very little pressure differential. Forces in excess of 1 atm may result in breakage, and pressure differentials of less magnitudes may cause permanent stretching of the membranes 146, 152 which may result in audio distortion, such as a kazoo effect. In one embodiment, the total microphone fixed volume is as small as practical which reduces vibration of the acoustic membrane 146 which causes kazoo effect distortion and noise during speaking using the communications system 10.

In one embodiment, acoustic membrane 146 operates to pass sound pressure waves which are within the voice chamber 14 to the airway 148 and microphone capsule 142, and to allow air to enter or leave the collapsible air chamber 144 as needed. Membrane 152 also functions to pass air into or out of the collapsible air chamber as needed. The collapsible air chamber 144 is inflated to full volume if the system 10 is to be taken down to the maximum design depth (e.g., 130-150 ft.) The membranes 146, 152 both allow air to refill the collapsible air chamber 144 when at any depth whenever the user has cleared the voice chamber 14 of water. The user may clear the voice chamber 14 of water while submerged if they want to descend past the design depth of the system 10. In addition, the membranes 146, 152 allow air to escape the collapsible air chamber 144, for example, if the system 10 is taken on a high altitude aircraft, placed in a hot car, or when ascending a body of water after using the system 10 at depth. The membranes 146, 152 allow air to enter to refill the collapsible air chamber 144 whenever the unit descends in an aircraft or the temperature drops. This passage of air prevents the acoustic membrane 146 from stretching or breaking and maintains quality audio reproduction by the microphone capsule 142.

First surfaces of membranes 146, 152 contact water within the voice chamber 14. In one embodiment, the collapsible air chamber 144 operates as a pressure control system which has different volumes and provides different pressures to a second, opposing surfaces of membranes 146, 152 as the assembly 17 is submerged to different depths.

As the diver and system 10 descend in the water column and pressure increases, the collapsible air chamber 144 which is exposed to increasing pressures of water within voice chamber 14 supplies air molecules to fill the microphone fixed volume space behind the back sides of the membranes 146, 152 as the pressure of the water within the voice chamber 14 increases. To do this, the collapsible air chamber 144 shrinks in volume also due to the increased forces exerted by the water and supplies the molecules of air to the microphone fixed volume space to increase the pressure of the air therein providing the increased pressures imposed upon membranes 146, 152.

Membrane 152 acts as a redundant pressure equalization membrane to membrane 146 and is used for extra insurance to allow air to enter from the voice chamber 14 or to vent excess air to the voice chamber 14. This is a redundant function/insurance as the acoustic membrane 146 also performs this function.

Accordingly, in one embodiment, collapsible air chamber 144 and the close proximity of the chamber 144 to the semi-permeable membranes 146, 152 operate to reduce the possible pressure differential experienced by the membranes 144, 152 and audio distortion. Membranes 146, 152 allow air to pass from the voice chamber 14 into the collapsible air chamber 144 if the internal pressure of the chamber 144 is (slightly) lower than the voice chamber 14 and air is present within the voice chamber 14 on the outside of the membranes 146, 152. This is the case when the chamber 144 is partially collapsed and there is air in the voice chamber 14.

Conversely, membranes 146, 152 also vent excess air from the collapsible air chamber 144 to voice chamber 14 if the pressure inside chamber 144 is greater than the pressure in the voice chamber 14. This is the case when ascending in the water with the collapsible air chamber 144 fully inflated. This passage of air through the membranes 146, 152 ensures that substantially equal pressures are maintained on both sides of the membranes 146, 152.

The membranes 146, 152 do not allow air to pass to the voice chamber 14 if there is water within voice chamber 14 outside of the membranes 146, 152 in one implementation. In some embodiments, the membranes 146, 152 may be located in close proximity (due to the small size of the entire microphone assembly 17) to the collapsible air chamber 144, and the pressures applied to the membranes 146, 152 and chamber 144 are nearly equal when water is present in chamber 14.

Since water is present in the voice chamber 14 during a descent, membranes 146, 152 prevent the escape of air into voice chamber 14 as the communication system 10 descends into the water column, and retains the air in the microphone body 140, capsule 142 and chamber 144. The chamber 144 is compressed as the user descends which increases the pressure on the back side of the membranes 146, 152 and which corresponds to the increased pressure on the front side of the membranes 146, 152 exposed to the water. This embodiments provides substantially equal pressures on both sides of membranes 146, 152 which prevent damage during descent. Additional air is needed to be supplied by chamber 144 as the user descends further. With proper volume sizing of chamber 144 (i.e., large enough for the maximum depth of use), the membranes 146, 152 do not see a significant pressure differential thereby avoiding damage.

Collapsible air chamber 144 is configured in the absence of external forces to expand to its full internal volume in one embodiment. The air chamber shape allows it to nearly fully collapse when the external pressure increases and to re-inflate to near full volume easily with very little pressure differential from inside to outside. The walls 164 of the collapsible air chamber 144 may be thin for quality audio and cast using liquid silicone rubber in one embodiment. The walls of collapsible air chamber 144 may have a thickness of 0.1 to 1 mm, with a specific thickness of 0.2 mm in one more specific embodiment. In addition, chamber 144 is cylindrical with a diameter of 25 mm and length of 25 mm and a total volume of approximately 12,000 cubic millimeters in one embodiment. Chamber 144 acts as a balloon with stiffening ribs 145 that act to restore the volume 168 of chamber 144 to fully inflated when air is available in the front of the acoustic and/or pressure equalization vents 146, 150 in one embodiment.

In the ranges of temperatures and pressures that the communication system 10 is typically used, the Ideal Gas Law (i.e., (pressure×volume)/temperature=a constant, with temperature in Kelvin) is accurate. According to the Ideal Gas Law, pressure goes up as one descends into the water column and a volume must decrease proportionally if the temperature stays the same. As diving is usually conducted in water between 35 degrees Fahrenheit (256 K) and 85 degrees Fahrenheit (303 K), or an 18% increase, temperature does not have much of an effect, and temperature is usually insignificant when the system 10 is in use.

In one embodiment, the volume of air chamber 144 varies according to the Ideal Gas Law (Pressure×Volume/Temperature=a constant) to maintain equal pressure on both sides of membranes 146, 152 when the system 10 is submerged in water and which protects the membranes 146, 152 from damage due to increasing water pressure on the outside of the membranes 146, 152 when descending.

Any flexible air chamber, such as a balloon or a diver's lungs, holds a certain volume when fully inflated. As one sits on the surface of the ocean, the pressure is one atmosphere (1 ATM). If the diver descends 33 feet, the pressure of the water exerts an additional 1 ATM of pressure, so the pressure is 2 ATM at 33 feet deep and volumes are collapsed to approximately one half of their volume at the surface of the water. If the diver descends further to 66 feet, the pressure of the water increases to 3 ATM and volumes are collapsed to approximately one third of their volume at the surface of the water. At the limits of recreational scuba diving (130 feet), the pressure is 5 ATM and volumes are collapsed to approximately one fifth their volume at the surface of the water. Accordingly, any submerged air spaces should have sufficient ability to collapse, or have air replaced from another source, or they could be crushed by the pressure at depth.

The pressure difference in water between one point and another one inch below can be significant. Any large flexible chamber will tend to stay full at the highest point, while the lower area will be collapsed by the pressure difference, forcing all the air to the top.

In one embodiment, a desiccant capsule 158 is an option within the air chamber 144 to collect water vapor molecules that pass thru the membranes 146, 152. In heavy use without time to dry out, the desiccant capsule 158 prevents an excessive amount of moisture from building up inside the airways 148, 150, microphone capsule 142 and chamber 144. Capsule 158 is accessed and sealed from the exterior via an access door 159 in the illustrated embodiment. Additionally, the communication system 10 may be allowed to dry between uses. Further, it may be beneficial to include a color change desiccant capsule that the user can replace if it gets saturated.

Referring to FIGS. 12A-12C, another embodiment of a microphone assembly 17a is shown. Similar to the assembly 17 of FIGS. 11A-11F, assembly 17a includes a body 140 housing microphone capsule 142, airways 148, 150, capsule 158 and door 159.

In addition, microphone assembly 17a further includes a second configuration of a pressure control system in the form of a manually compressible flexible chamber 170 which is a squeeze bulb in the illustrated embodiment. Chamber 170 is an alternative air source to the air chamber 144 described above and deflates when squeezed by hand and re-inflates itself when hand pressure is removed.

Further, chamber 170 is also exposed to water pressure from the body of water. In one implementation, the chamber 170 is provided external of the voice chambers 14, 16 in a place accessible by the user during diving for manipulation and is held at a slightly lower depth below the microphone capsule 142 during use. As discussed below, the chamber 170 causes air to flow through membranes 146, 152 and imparts tension thereto which may reduce distortion.

In one embodiment, chamber 170 provides the function of chamber 144 described above to act as an air reservoir with additional air molecules which adjusts pressure on the internal sides of membranes 146, 152 as the diver submerges or ascends to keep the pressure nearly balanced on both sides of membranes 146, 152. There is a fixed quantity of air within the microphone assembly 17a when water is present within the voice chamber 14 as was described in FIGS. 11A-11F, and chamber 170 varies the pressure of the air to apply the different pressures to the membranes 146, 152 in one embodiment. If volume 168 of chamber 144 is filled with air during an ascent by the user, air from volume 168 is released via the membranes 146, 152 and substantially equal pressures are maintained on both surfaces of each of the membranes 146, 152.

Chamber 170 may also be used to provide a substantially constant air flow thru the acoustic membrane 146 while speaking by squeezing and/or releasing the chamber 170 which provides a flow of air into or out of chamber 170 via connection tube 172 as well as tension to membranes 146, 152. The air flowing in or out thru the acoustic membrane 146 while speaking prevents or reduces vibrations of membrane 146 the associated audio distortion kazoo effect. The membranes 146, 152 are held taut by the slight difference in pressure between the airways 148, 150 and the air pressure inside the voice chamber 14.

Before a dive, the chamber 170 is totally inflated as it fills with air that is pulled in thru the membranes 146, 152. Chamber 170 can be squeezed and released, providing air flow through the acoustic membrane 146 when the user is speaking, or constantly squeezed while speaking and the air will flow out thru the acoustic membrane 146. Either direction of flow will provide a small tension force on the membrane 146 and will prevent or reduce vibration which may otherwise produce noise which passes into the microphone capsule 142 and interferes with the voice signal.

In one embodiment, the volume of the chamber 170 is greater than five times the volume of the airspace of airways 148, 150, 174 and tube 172 to assure there is sufficient air to maintain pressure equilibrium across membranes 146, 152 for a maximum diving depth of 130 feet.

Using this embodiment is nearly the same as other embodiments of this device with a few additional functions that the user performs. As the diver descends, chamber 170 gradually collapses by the increasing water pressure. When the diver is ready to use the device, they will follow the same procedure as other embodiments—that is, bring the device up to and seal against their face, blow a puff of air into the voice chamber 14 which fills voice chambers 14, 16 with air, turn the device on, and begin speaking. The front side of the membranes 146, 152 are now exposed to air and chamber 170 draws air through the membranes 146, 152 and there will be a slight pressure difference across the membranes 146, 152, which will keep them taut. When the chamber 170 fills completely and the user wishes to talk, the user will then need to apply gentle pressure to the chamber 170 which causes a pressure difference in the opposite direction as before. When the chamber 170 is nearly empty, the user releases the chamber 170, and the pressure difference switches so that now there is slightly lower pressure in the airways 148, 150, and the membranes 146, 152 remain taut.

Figure 13:
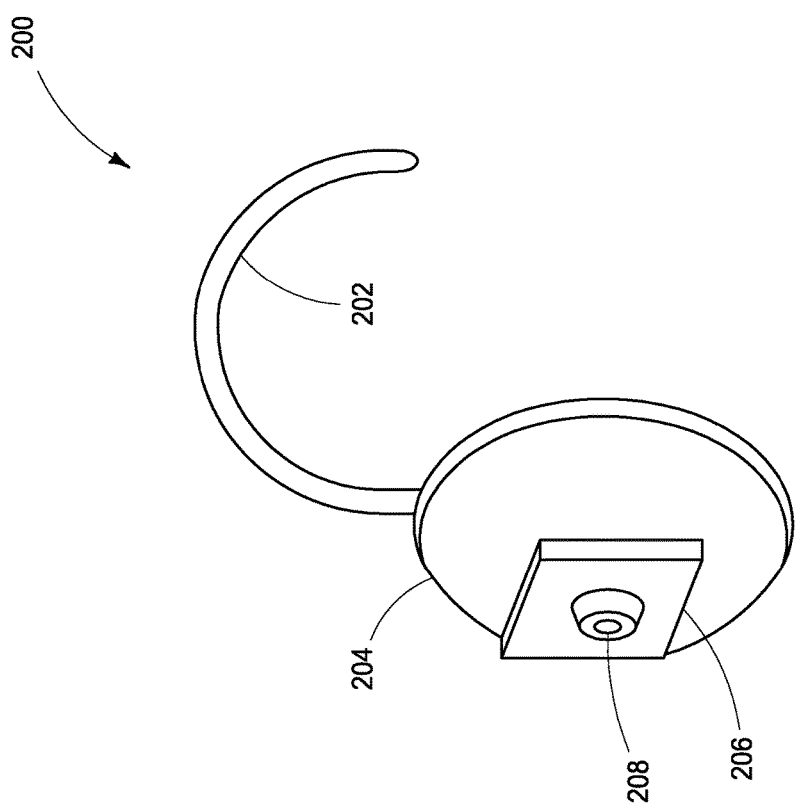
FIG. 13 is a perspective view of a receiver assembly according to one embodiment.

Referring to FIG. 13, a receiver assembly 200 is shown which may be worn by other divers underwater who wish to hear the operator of the communications system 10. The receiver assembly 200 includes a headband 202 for attachment to the head of the user, an ear cup 204, a battery and amplifier compartment 206 and a hydrophone 208.

The receiver assembly 200 allows a diver to more easily hear the sound transmission of the above described communication system 10 and speakers 20, such as when at a farther distance from the speaking diver. In one embodiment, the hydrophone 208 outputs electrical signals responsive to received sound pressure waves and which are amplified by an amplifier (not shown) within compartment 206 and which may be powered by the respective battery. The amplifier amplifies all sounds in the water received by hydrophone 208 including the output of speakers 20 described above. The amplified signals are provided to the speaker within the ear cup 204 for listening by the user.

Some of the audio that the hydrophone 208 receives may be filtered using electronic circuitry (digital or analog). For example, regulator exhaled air noise may be significantly reduced by filtering out the frequencies generated by this source. In addition, sound level limiting circuitry may be used to limit the output sound level to a safe and comfortable level for the listening diver.

Maintenance of some embodiments of the communication system is relatively straightforward including recharging the batteries, rinse after using in sea water, and possibly change the desiccant capsule in the microphone assembly.

As discussed above, the speakers and associated circuitry may be used as pool speakers, or underwater speakers for other applications such as diver recall systems, military underwater disorientation devices, fish attractor systems or diver warning systems in additional example implementations.

In some embodiments, the communication system may include an audio recorder to record audio during a dive, for example, into a first in first out buffer. This would be useful when doing work that would normally require taking notes on a dive slate. This could also be used for taking fish count surveys (e.g., REEF.org, the Audubon of the Sea, promotes divers to become trained in identifying fish species, and maintains the world's largest online database of fish sightings). This example of the communication system would make surveying easier and more accurate compared with other methods, as it is sometimes difficult to remember fish names, and identifying features could be recorded for later lookup to positively identify the species.

In one embodiment, an emergency SOS mode may be provided where the communication device generates a "siren" sound and flashes lights to alert other divers that the user needs help.

In one embodiment, a fish attractor mode may be provided where the communication device generates sound pressure waves which attract fish (e.g., used to attract the invasive Lionfish).

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended aspects appropriately interpreted in accordance with the doctrine of equivalents.

Further, aspects herein have been presented for guidance in construction and/or operation of illustrative embodiments of the disclosure. Applicant(s) hereof consider these described illustrative embodiments to also include, disclose and describe further inventive aspects in addition to those explicitly disclosed. For example, the additional inventive aspects may include less, more and/or alternative features than those described in the illustrative embodiments. In more specific examples, Applicants consider the disclosure to include, disclose and describe methods which include less, more and/or alternative steps than those methods explicitly disclosed as well as apparatus which includes less, more and/or alternative structure than the explicitly disclosed structure.

What is claimed is:

1. An underwater communication system comprising:
   a voice chamber assembly configured to receive first sound pressure waves from a user;
   a microphone assembly within the interior volume of the voice chamber and configured to convert the first sound pressure waves received within the interior volume of the voice chamber into electrical signals which correspond to the first sound pressure waves;
   a speaker electrically coupled with the microphone assembly and comprising a transducer member configured to emit second sound pressure waves into a body of water corresponding to the first sound pressure waves received within the voice chamber;
   a pressure control system which is configured to impart increasing pressure to the transducer member corresponding to increasing depth of the speaker in the body of water; and
   wherein the pressure control system comprises a bladder configured to receive water from the body of water.

2. The system of claim 1 wherein the bladder comprises a plurality of acoustic vents configured to emit the sound pressure waves.

3. The system of claim 1 wherein the bladder comprises an external opening which is configured to receive air and to expel water from the bladder.

4. The system of claim 1 wherein the bladder is configured to receive the water into an internal volume of the bladder.

5. An underwater communication system comprising:
   a voice chamber assembly configured to receive first sound pressure waves from a user;
   a microphone assembly within the interior volume of the voice chamber and configured to convert the first sound pressure waves received within the interior volume of the voice chamber into electrical signals which correspond to the first sound pressure waves;
   a speaker electrically coupled with the microphone assembly and configured to emit second sound pressure waves into a body of water corresponding to the first sound pressure waves received within the voice chamber;
   wherein the microphone assembly comprises:
      an input airway;
      an acoustic membrane which is impervious to water and configured to prevent water from the body of water in which the communication system is submerged from entering the input airway and to pass air molecules of the first sound pressure waves into the input airway;

a microphone configured to receive the first sound pressure waves from the input airway and to generate the electrical signals which correspond to the first sound pressure waves; and a pressure control system configured to apply different pressures to the acoustic membrane which correspond to different depths of the communication system within the body of water.

6. The system of claim 5 wherein a first surface of the acoustic membrane contacts the water from the body of water and the pressure control system is configured to provide the different pressures to a second surface of the acoustic membrane which is opposite to the first surface.

7. The system of claim 5 wherein the pressure control system comprises a collapsible air chamber which is exposed to water of the body of water and configured to have different volumes at different depths within the body of water, and to increase the pressure of air within the input airway as a result of the microphone assembly being submerged to a lower depth within the body of water.

8. The system of claim 5 wherein the pressure control system comprises a squeeze bulb which is configured to cause air to flow through the acoustic membrane as a result of user manipulation and to impart tension to the acoustic membrane.

9. The system of claim 5 wherein the microphone assembly comprises a fixed quantity of air, and the pressure control system is configured to vary pressure of the air to apply the different pressures.

10. The system of claim 5 wherein the microphone assembly includes a microphone fixed volume space which has a volume which is less than or equal to 200 cubic millimeters.

* * * * *